(12) United States Patent
Fedorov et al.

(10) Patent No.: US 9,693,761 B2
(45) Date of Patent: Jul. 4, 2017

(54) RETRACTOR DEVICE AND METHOD

(71) Applicant: Blackstone Medical, Inc., Lewisville, TX (US)

(72) Inventors: Sergey Fedorov, Plano, TX (US); Jesse Moore, Frisco, TX (US); Mark Evald Semler, McKinney, TX (US); Jose Luis Charvet, Fairfield, NJ (US)

(73) Assignee: Blackstone Medical, Inc., Lewisville, TX (US)

( * ) Notice: Subject to any disclaimer, the term of this patent is extended or adjusted under 35 U.S.C. 154(b) by 0 days.

(21) Appl. No.: 13/659,673

(22) Filed: Oct. 24, 2012

(65) Prior Publication Data

US 2014/0114138 A1    Apr. 24, 2014

(51) Int. Cl.
*A61B 1/32* (2006.01)
*A61B 17/02* (2006.01)
*A61B 17/00* (2006.01)

(52) U.S. Cl.
CPC ...... *A61B 17/0206* (2013.01); *A61B 17/0293* (2013.01); *A61B 2017/00407* (2013.01)

(58) Field of Classification Search
CPC . A61B 17/02; A61B 17/0206; A61B 17/0218; A61B 17/025; A61B 17/0293; A61B 17/32; A61B 17/3421; A61B 17/3423; A61B 17/3439; A61B 2017/0256; A61B 2017/00407
USPC ................................. 600/184–249
See application file for complete search history.

(56) References Cited

U.S. PATENT DOCUMENTS

| | | | |
|---|---|---|---|
| 1,428,653 A | 9/1922 | Nick | |
| 2,083,573 A * | 6/1937 | Morgan | 600/224 |
| 2,594,086 A | 4/1952 | Smith | |
| 3,965,890 A | 6/1976 | Gauthier | |
| 4,130,113 A | 12/1978 | Graham | |
| 4,942,700 A | 7/1990 | Hoberman | |
| 5,024,031 A | 6/1991 | Hoberman | |
| 5,081,983 A | 1/1992 | Villalta et al. | |
| 5,125,396 A | 6/1992 | Ray | |
| 5,183,032 A * | 2/1993 | Villalta et al. | 600/224 |
| 5,377,667 A * | 1/1995 | Patton | A61B 1/32 |
| | | | 600/184 |
| 5,505,690 A * | 4/1996 | Patton et al. | 600/210 |
| 5,509,893 A * | 4/1996 | Pracas | A61B 1/32 |
| | | | 600/184 |
| 5,657,584 A | 8/1997 | Hamlin | |
| 5,846,249 A | 12/1998 | Thompson | |
| 5,944,658 A | 8/1999 | Koros et al. | |
| 6,096,046 A | 8/2000 | Weiss | |
| 6,206,828 B1 * | 3/2001 | Wright | 600/232 |

(Continued)

OTHER PUBLICATIONS

International Search Report and Written Opinion, PCT/US2013/066628, dated Dec. 23, 2013, 10 pages.

(Continued)

*Primary Examiner* — Eduardo C Robert
*Assistant Examiner* — Michelle C Eckman
(74) *Attorney, Agent, or Firm* — Baker & McKenzie LLP

(57) ABSTRACT

The present disclosure generally relates to a retractor device for retracting soft tissue to provide access to a surgical site. The retractor device includes a plurality of blades movable from a first, substantially closed position to a second, substantially open position. Related methods of using the retractor device are also described.

23 Claims, 25 Drawing Sheets

(56) References Cited

U.S. PATENT DOCUMENTS

| | | |
|---|---|---|
| 6,280,379 B1 | 8/2001 | Resnick |
| 6,342,036 B1 | 1/2002 | Cooper et al. |
| 6,354,995 B1 * | 3/2002 | Hoftman et al. ............. 600/219 |
| 6,416,468 B2 | 7/2002 | Deckman et al. |
| 6,440,064 B1 | 8/2002 | Rehm |
| 6,613,038 B2 | 9/2003 | Bonutti et al. |
| 6,746,396 B1 | 6/2004 | Segermark et al. |
| 7,182,730 B2 * | 2/2007 | Fehling .................. 600/224 |
| 7,195,592 B2 * | 3/2007 | Ravikumar et al. .......... 600/219 |
| 7,344,495 B2 * | 3/2008 | Ravikumar et al. .......... 600/219 |
| 7,374,534 B2 | 5/2008 | Dalton |
| 7,435,219 B2 | 10/2008 | Kim |
| 7,491,168 B2 * | 2/2009 | Raymond et al. ............ 600/231 |
| 7,537,565 B2 | 5/2009 | Bass |
| 7,556,600 B2 | 7/2009 | Landry et al. |
| 7,594,888 B2 | 9/2009 | Raymond et al. |
| 7,722,570 B2 | 5/2010 | Almond et al. |
| 7,758,501 B2 | 7/2010 | Frasier et al. |
| 7,780,594 B2 | 8/2010 | Hutton |
| 7,850,608 B2 | 12/2010 | Hamada |
| 7,892,174 B2 | 2/2011 | Hestad et al. |
| 7,931,589 B2 | 4/2011 | Cohen et al. |
| 7,935,053 B2 | 5/2011 | Karpowicz et al. |
| 7,981,031 B2 | 7/2011 | Frasier et al. |
| 7,985,179 B2 | 7/2011 | Gephart et al. |
| 8,038,611 B2 | 10/2011 | Raymond et al. |
| 8,062,217 B2 | 11/2011 | Boucher et al. |
| 8,075,482 B2 * | 12/2011 | Beckman ........... A61B 17/3462 600/208 |
| 8,083,673 B2 | 12/2011 | Rosen |
| 8,105,236 B2 | 1/2012 | Malandain et al. |
| 8,152,721 B2 * | 4/2012 | Michaeli et al. ............. 600/224 |
| 8,182,519 B2 | 5/2012 | Loftus et al. |
| 8,192,463 B2 | 6/2012 | McLoughlin |
| 8,211,012 B2 | 7/2012 | Wing et al. |
| 8,262,570 B2 | 9/2012 | White et al. |
| 8,267,859 B2 | 9/2012 | Holmes |
| 8,303,499 B2 | 11/2012 | Hamada |
| 8,317,692 B2 | 11/2012 | Loftus et al. |
| 8,353,826 B2 | 1/2013 | Weiman |
| 2001/0041828 A1 | 11/2001 | Deckman et al. |
| 2002/0072713 A1 | 6/2002 | Almond et al. |
| 2003/0088157 A1 | 5/2003 | Vassiliades, Jr. et al. |
| 2004/0087833 A1 * | 5/2004 | Bauer et al. .................. 600/201 |
| 2004/0176665 A1 | 9/2004 | Branch et al. |
| 2005/0070765 A1 | 3/2005 | Abdelgany et al. |
| 2005/0080320 A1 | 4/2005 | Lee et al. |
| 2005/0159651 A1 | 7/2005 | Raymond et al. |
| 2005/0165281 A1 * | 7/2005 | Ravikumar et al. .......... 600/204 |
| 2005/0203347 A1 | 9/2005 | Fehling |
| 2005/0215866 A1 | 9/2005 | Kim |
| 2005/0277812 A1 | 12/2005 | Myles |
| 2006/0052672 A1 | 3/2006 | Landry et al. |
| 2006/0142643 A1 | 6/2006 | Parker |
| 2006/0178566 A1 | 8/2006 | Fetzer |
| 2007/0010716 A1 | 1/2007 | Malandain et al. |
| 2007/0038033 A1 | 2/2007 | Jones et al. |
| 2007/0156024 A1 | 7/2007 | Frasier et al. |
| 2007/0156025 A1 | 7/2007 | Marchek et al. |
| 2007/0156026 A1 | 7/2007 | Frasier et al. |
| 2007/0203399 A1 | 8/2007 | Gephart et al. |
| 2007/0238932 A1 | 10/2007 | Jones et al. |
| 2007/0282171 A1 | 12/2007 | Karpowicz et al. |
| 2008/0183046 A1 | 7/2008 | Boucher et al. |
| 2008/0319268 A1 * | 12/2008 | Michaeli et al. ............. 600/202 |
| 2009/0018400 A1 | 1/2009 | Raymond et al. |
| 2009/0018401 A1 | 1/2009 | Kim |
| 2009/0069635 A1 | 3/2009 | Gephart et al. |
| 2009/0124861 A1 * | 5/2009 | Fetzer .................... A61B 90/50 600/226 |
| 2009/0158674 A1 | 6/2009 | Guerrero et al. |
| 2010/0069740 A1 | 3/2010 | Larson et al. |
| 2010/0081885 A1 | 4/2010 | Wing et al. |
| 2010/0160947 A1 | 6/2010 | Akyuz et al. |
| 2010/0274094 A1 | 10/2010 | Abdelgany et al. |
| 2011/0004067 A1 * | 1/2011 | Marchek et al. ............. 600/214 |
| 2011/0224496 A1 | 9/2011 | Weiman |
| 2011/0224497 A1 | 9/2011 | Weiman et al. |
| 2011/0237898 A1 | 9/2011 | Stone et al. |
| 2011/0245621 A1 | 10/2011 | Frasier et al. |
| 2011/0301421 A1 * | 12/2011 | Michaeli ............ A61B 17/0293 600/211 |
| 2011/0301423 A1 | 12/2011 | Koros et al. |
| 2011/0313256 A1 | 12/2011 | Raymond et al. |
| 2012/0046527 A1 | 2/2012 | Cianfrani et al. |
| 2012/0101341 A1 | 4/2012 | Malandain et al. |
| 2012/0165613 A1 | 6/2012 | Loftus et al. |
| 2012/0172669 A1 | 7/2012 | Loftus et al. |
| 2012/0172670 A1 | 7/2012 | Hamada |
| 2012/0190935 A1 | 7/2012 | Loftus et al. |
| 2012/0245432 A1 | 9/2012 | Karpowicz et al. |
| 2013/0066161 A1 | 3/2013 | Wenchell |

OTHER PUBLICATIONS

International Search Report and Written Opinion, PCT/US2014/055681, dated Dec. 16, 2014, 8 pages.

U.S. Appl. No. 14/030,546, Non-Final Office Action, dated Jul. 22, 2014, 111 pages.

Final Office Action, U.S. Appl. No. 14/030,546, dated Aug. 11, 2016, 18 pages.

* cited by examiner

RETRACTOR DEVICE AND METHOD

TECHNICAL FIELD

The present disclosure generally relates to the field of orthopedics and spinal surgery, and more particularly, to retractor devices for use in surgery. Related methods are also described.

BACKGROUND

In the treatment of diseases, injuries or malformations affecting spinal motion segments, and especially those affecting disc tissue, it has long been known to remove some or all of a degenerated, ruptured or otherwise failing disc. In cases involving intervertebral disc tissue that has been removed or is otherwise absent from a spinal motion segment, corrective measures are taken to ensure the proper spacing of the vertebrae formerly separated by the removed disc tissue.

Such corrective measures may include spinal fusion or insertion of a disc prosthesis into the disc space. Such surgical techniques require access to the surgical site through tissue. Invasive techniques may cause tissue necrosis and creep. Accordingly, devices and methods for reducing invasiveness associated with accessing a spinal surgical site are desired.

BRIEF SUMMARY

The present disclosure generally relates to a retractor device for tissue retraction. In some embodiments, a retractor device according to the present disclosure may include a pair of concentric rings that are coupled to one another, yet adapted to move circumferentially relative to one another. A plurality of arms are coupled to one or more of the rings and further include a plurality of associated blades extending in a direction substantially perpendicular to the plane of the rings. The arms may be removably attached to one or more of the rings such that the blades can be replaced while the device is in use. An actuator is coupled to the device to cause movement of the rings relative to one another, and a ratcheting mechanism may be used to provide for one-way rotation. Rotation of the rings relative to each other causes the blades to move from an initial, substantially closed position, to a second, substantially open position. The device may further include a release mechanism for enabling the blades to move from the open position back to the closed position. Related methods for using the retractor device are also described.

In other embodiments, a retractor device according to the present disclosure may include a plurality of linked appendages. Each linked appendage is coupled to an adjacent linked appendage such that the retractor device has a substantially symmetrical shape with a common axis when viewed in plan. The linked appendages further include a blade extending in a direction substantially parallel to the common axis and substantially perpendicular to the plane defined by the linked appendages. The linked appendages may be moved from a first, substantially closed position, to a second, substantially open position to thereby move the blades from a substantially closed position to a substantially open position. The linked appendages may be actuated in a variety of manners, including by handles extending from one of the linked appendages. Related methods for using the retractor device are also described.

In still further embodiments, a retractor device according to the present disclosure includes a pair of discs in which an upper disc rotates relative to a lower disc to actuate blades from a first, substantially closed position to a second, substantially open position. The upper disc is received onto posts extending from the lower disc via elongated slots defined through the upper disc. The retractor device further includes a plurality of blades, which include a mounting portion for coupling to the lower disc through channels defined in the lower disc. To facilitate coupling, the mounting portion includes a threaded post for receiving a correspondingly threaded nut of sufficient diameter to retain the mounting portion to the lower disc. Rotation of the upper disc causes translation of the mounting portions along the channels to thereby retract the blades into a desired position. Various tools may be used with the retractor device to retract the blades either independently or simultaneously. Additional tools may be used to lock the blades in place.

BRIEF DESCRIPTION OF THE DRAWINGS

Reference is now made to the following descriptions taken in conjunction with the accompanying drawings.

DETAILED DESCRIPTION

Various embodiments of a retractor device and methods of using such retractor devices according to the present disclosure are described. It is to be understood, however, that the following explanation is merely exemplary in describing the devices and methods of the present disclosure. Accordingly, several modifications, changes and substitutions are contemplated.

Figure 1A:
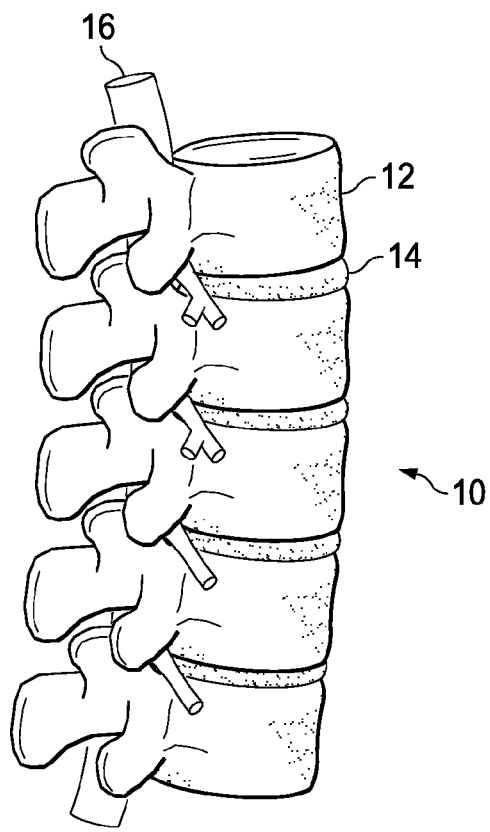
FIG. 1A illustrates a portion of a human spinal column.
Figure 1B:
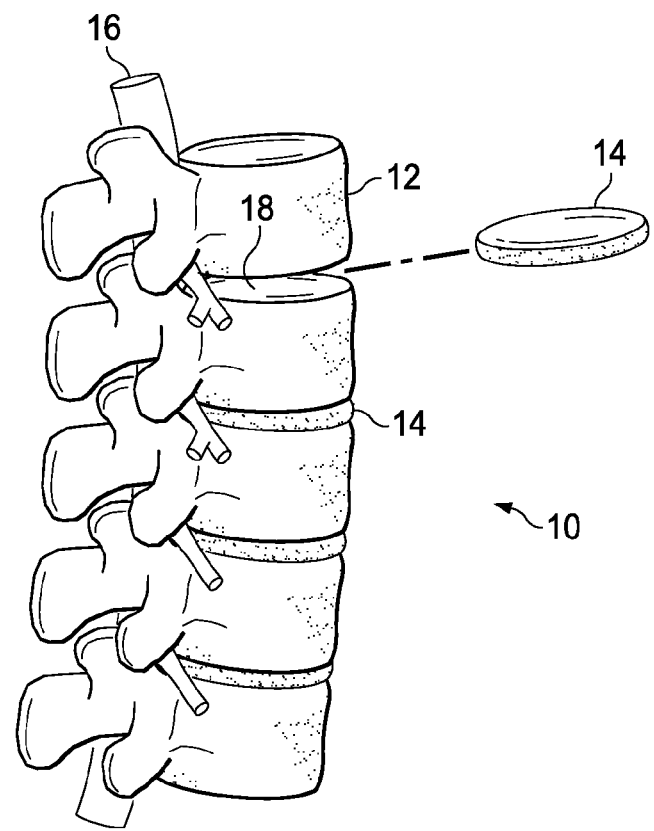
FIG. 1B illustrates a portion of a human spinal column with an intervertebral disc removed.

A portion of a human spinal column 10 is schematically illustrated in FIG. 1A and includes a series of vertebrae 12 intersected by a series of intervertebral discs 14. The vertebrae 12 generally encapsulate a spinal cord 16, which generally comprises nervous tissue and serves as the main pathway for information connecting the brain and peripheral nervous system. Referring to FIG. 1B, it sometimes becomes necessary to remove a diseased, or otherwise failing, intervertebral disc. Such procedures leave an intervertebral disc space 18 defined between adjacent vertebrae of the spinal column. Some surgical procedures call for fusion of the adjacent vertebrae 12, while other procedures may call for insertion of a prosthetic disc into the intervertebral disc space 18. In either scenario, or in additional spinal surgery scenarios, access to the intervertebral disc space 18 through tissue is required. According to the principles of the present disclosure, it is desirable to provide for minimally invasive access to the surgical site through such tissue.

A retractor device 20 according to some embodiments of the present disclosure is illustrated in FIGS. 2-8. The retractor device 20 is preferably used in surgical procedures involving the cervical and/or lumbar regions of the spinal column; however, the retractor device may be used in other surgical applications requiring distraction of tissue and such uses are contemplated as falling within the scope of the present disclosure. The retractor device 20 includes a frame 22, which includes a pair of concentric rings 24, 26, which are adapted to slide circumferentially relative to one another in a manner to be described. In some embodiments, the frame 22 includes an additional mounting ring 28. The retractor device 20 further includes a plurality of arm members 30, which include a mounting portion 32 for coupling to the frame 22 and a blade portion 34, which extends in a direction substantially perpendicular to a plane defined by the frame.

Figure 4A:
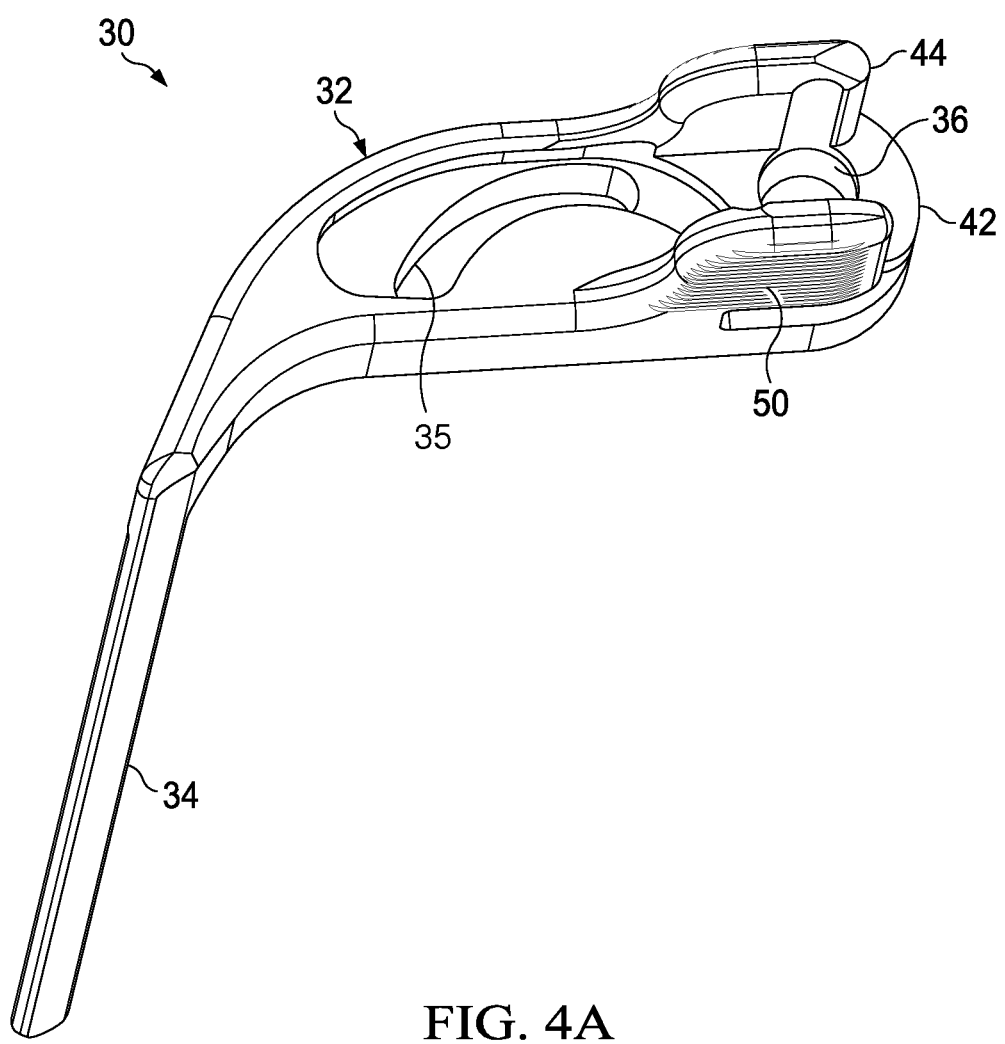
FIG. 4A illustrates a top perspective view of a blade of the retractor device of FIG. 2 according to one embodiment of the present disclosure.
Figure 4B:
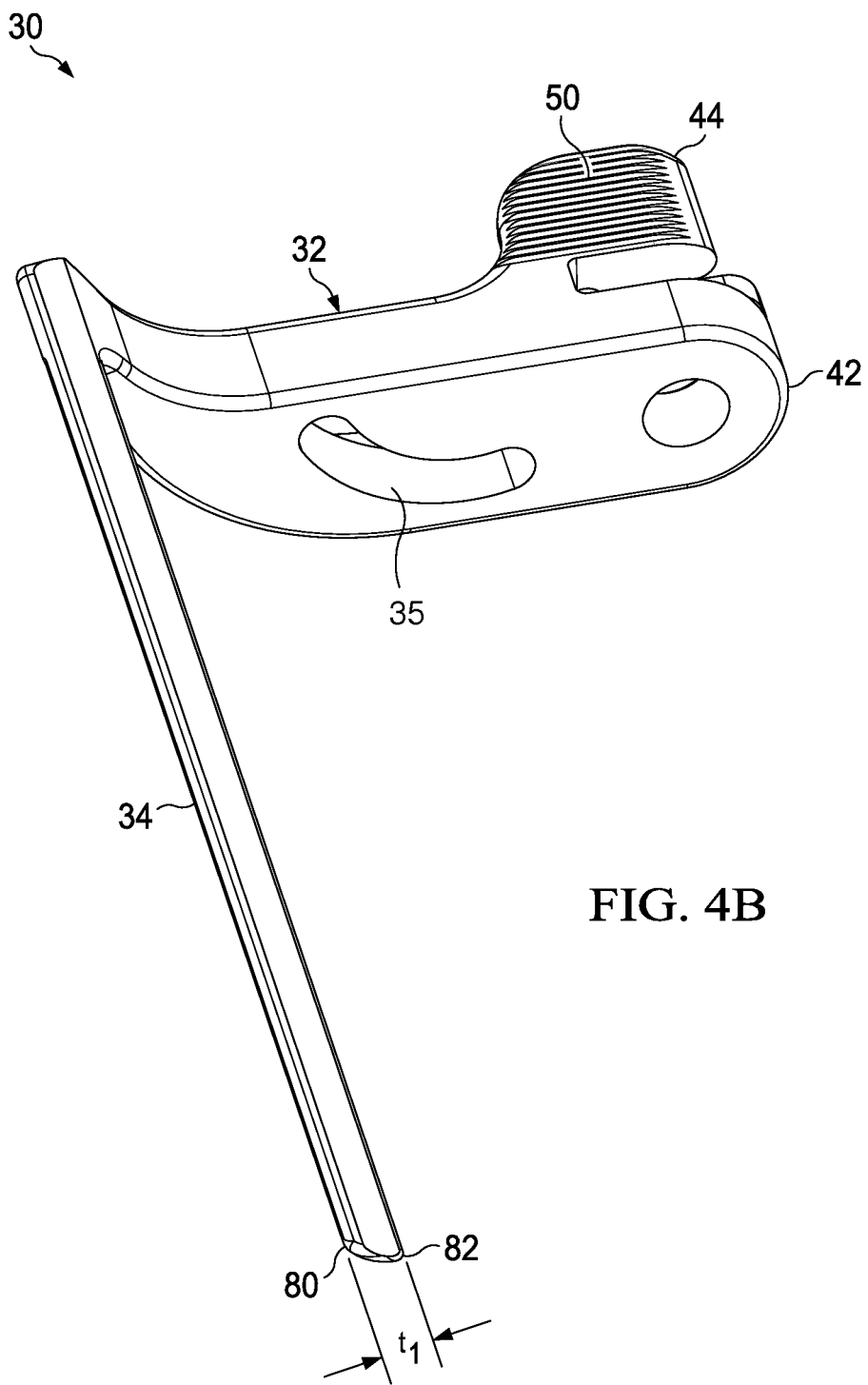
FIG. 4B illustrates a bottom perspective view of the blade of FIG. 4A.

With respect to one of the arm members 30 shown in detail in FIGS. 4A and 4B, the mounting portion 32 is adapted for coupling to the frame 22 via an elongated slot 35 and an eccentric hole 36 defined through the mounting portion. More particularly, and with reference to FIGS. 2 and 5, the inner ring 26 may include a peg-like element 38 disposed thereon for being received into the elongated slot 35 of the arm member 30. In some embodiments, the peg-like element 38 may be substantially cylindrical in shape, however, other configurations are contemplated so long a the peg-like element fits within and is adapted for moving along the elongated slot 35 as will be described. The outer ring 24 may include a plurality of mounting posts 40 for being received through the arm member 30 via the eccentric hole 36.

Figure 2:
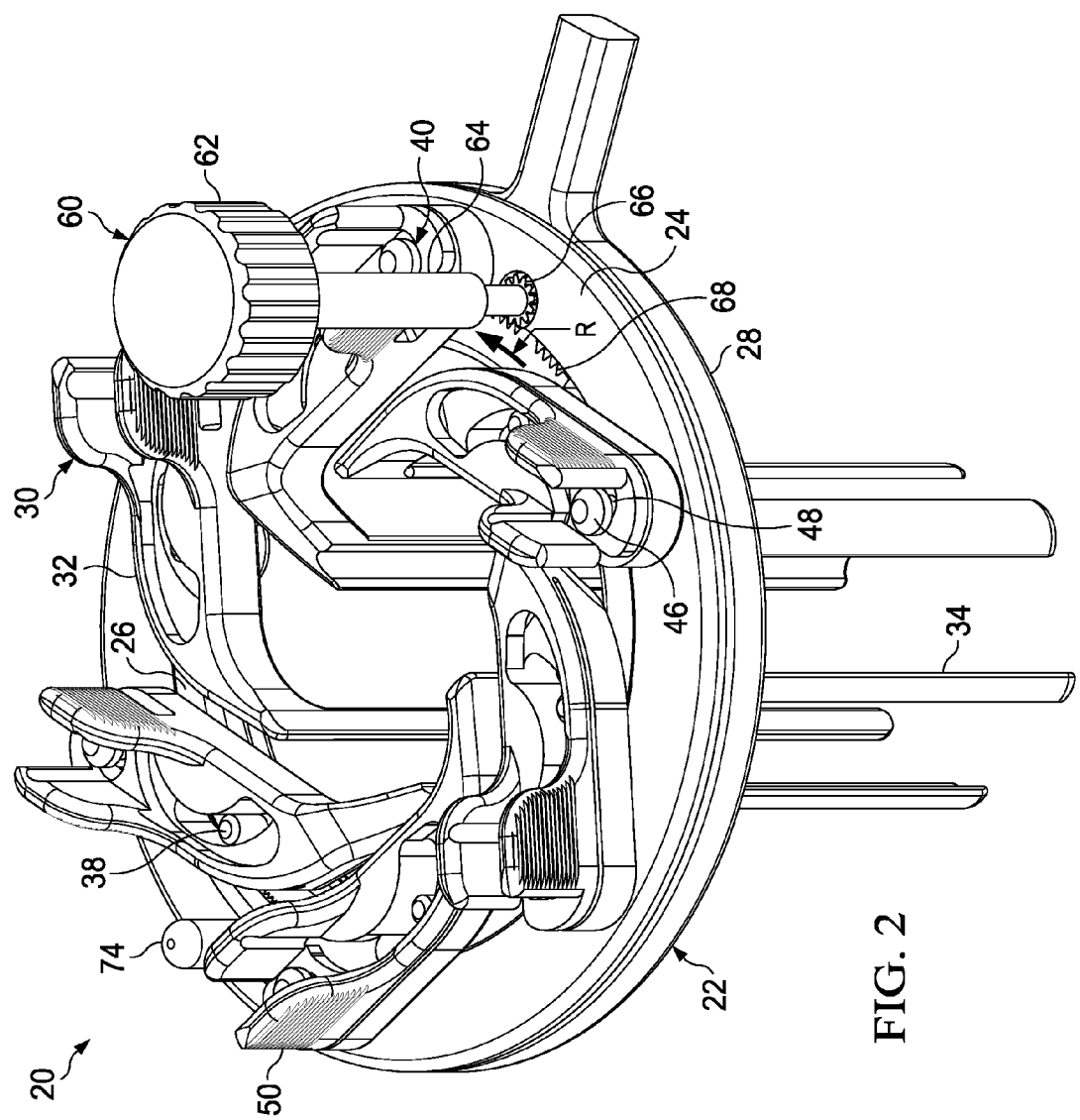
FIG. 2 illustrates a top perspective view of a retractor device according to one embodiment of the present disclosure.

Referring again to FIGS. 4A and 4B, the mounting portion 32 of the arm member 30 includes a spring-loaded latch member 42 as well as a pair of detents 44 to facilitate quick attachment and removal of the arm member 30 to the frame 22. To facilitate such attachment, the mounting post 40 may be stepped in diameter to include a larger head portion 46 relative to a shaft portion 48 (FIG. 2). In this manner, the spring loaded latch 42 is adapted to bear against the shaft portion to retain the arm member 30 in engagement with the frame 22. Such an arrangement further holds the arm member 30 in place in the vertical direction as the head portion 46 of the mounting post 40 will block removal of the arm member 30. Should removal of the arm member 30 from the frame 22 be desired, a user may engage the detents 44 to position the entirety of the mounting post 40 within the eccentric hole 36 and thereby remove the arm from the frame by lifting the arm off of the mounting post. In some embodiments, the detents 44 may include a ribbed portion 50 to facilitate gripping of the arm member 30 during insertion and/or removal.

Figure 3:
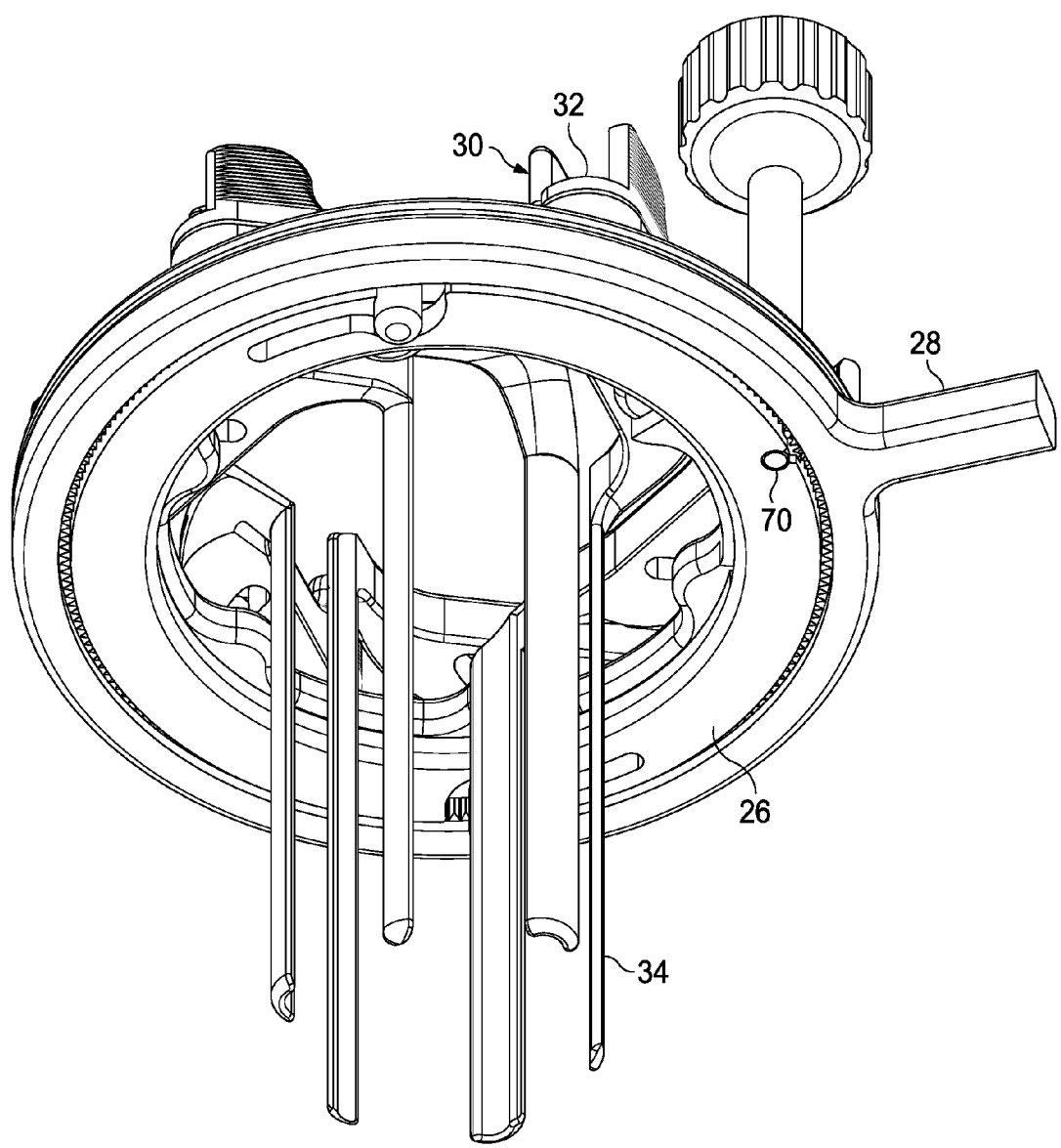
FIG. 3 illustrates a bottom perspective view of the retractor device of FIG. 2.
Figure 5:
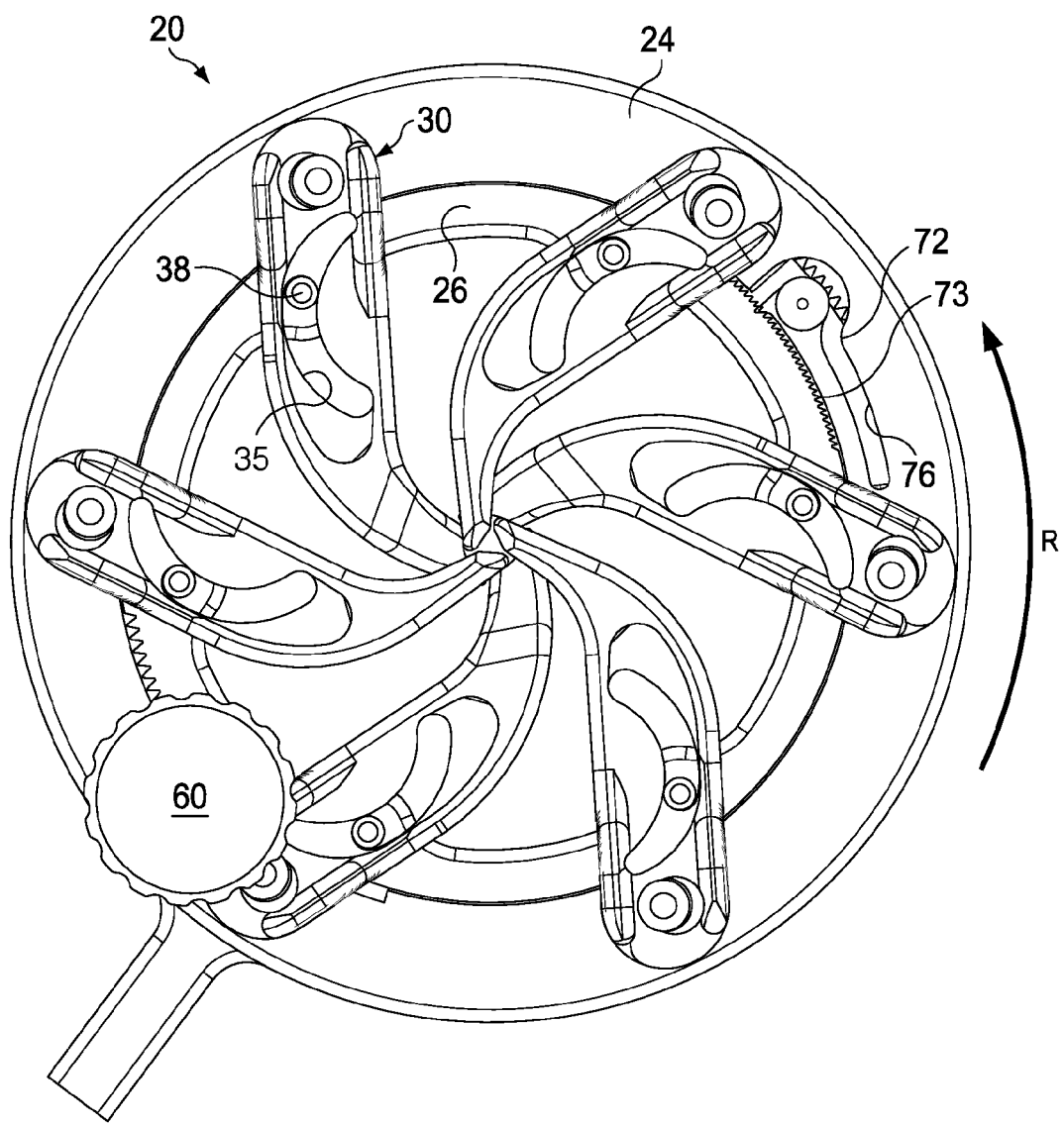
FIG. 5 illustrates a top view of the retractor device of FIG. 2 with the blades in a closed position.
Figure 6:
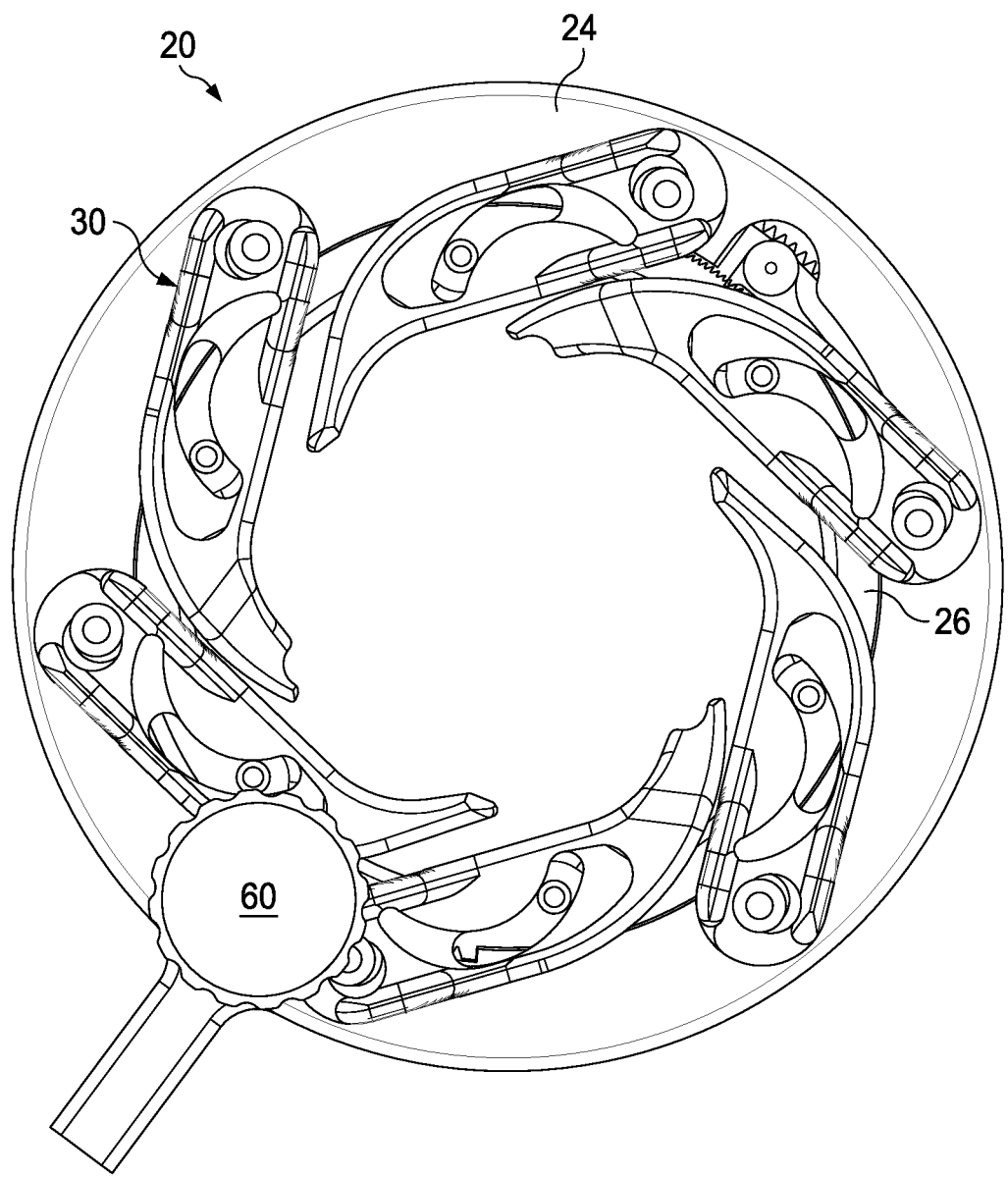
FIG. 6 illustrates a top view of the retractor device of FIG. 2 with the blades in an open position.
Figure 7:
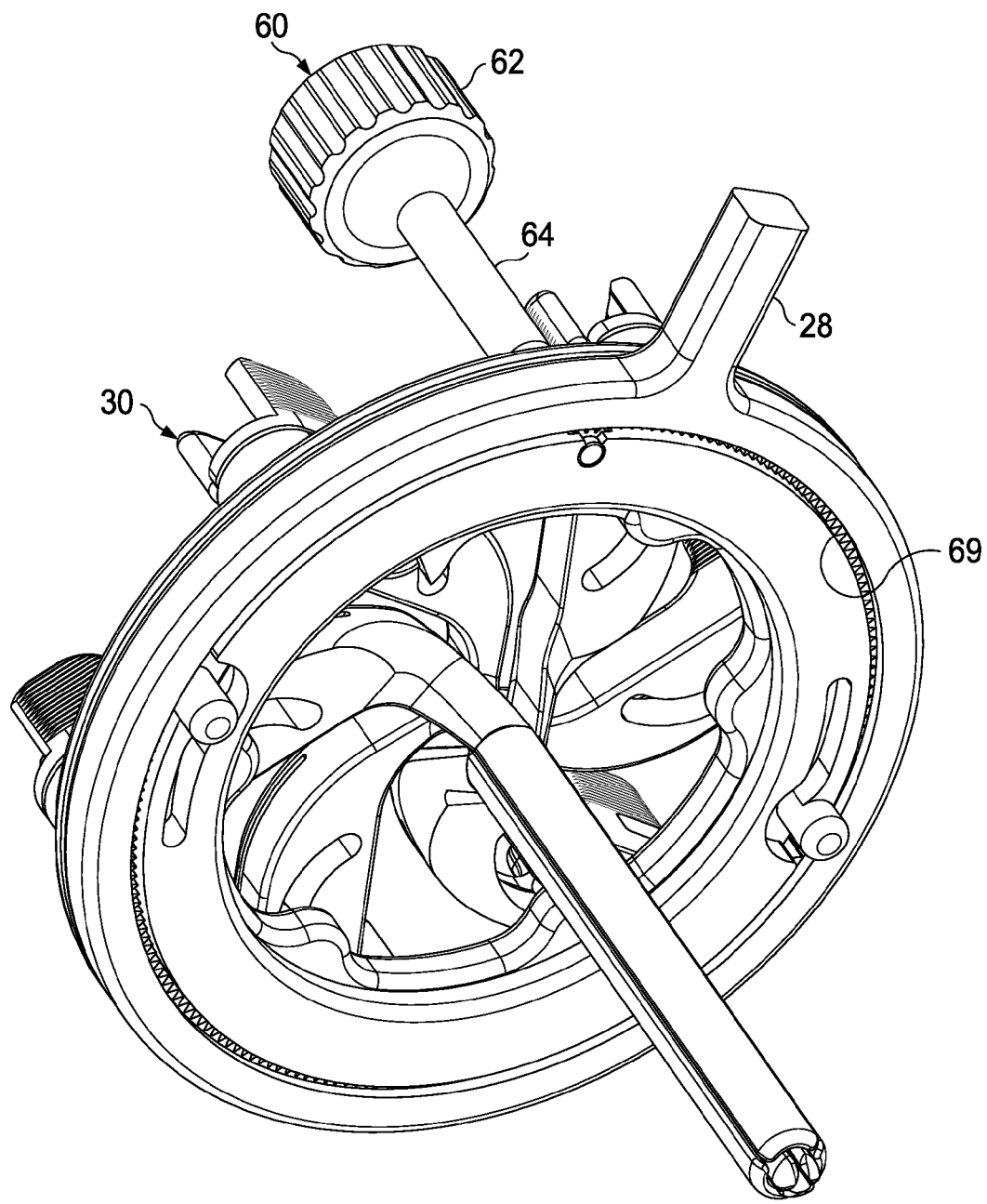
FIG. 7 illustrates a bottom perspective view of the retractor device of FIG. 2 with blades in a closed position.
Figure 8:
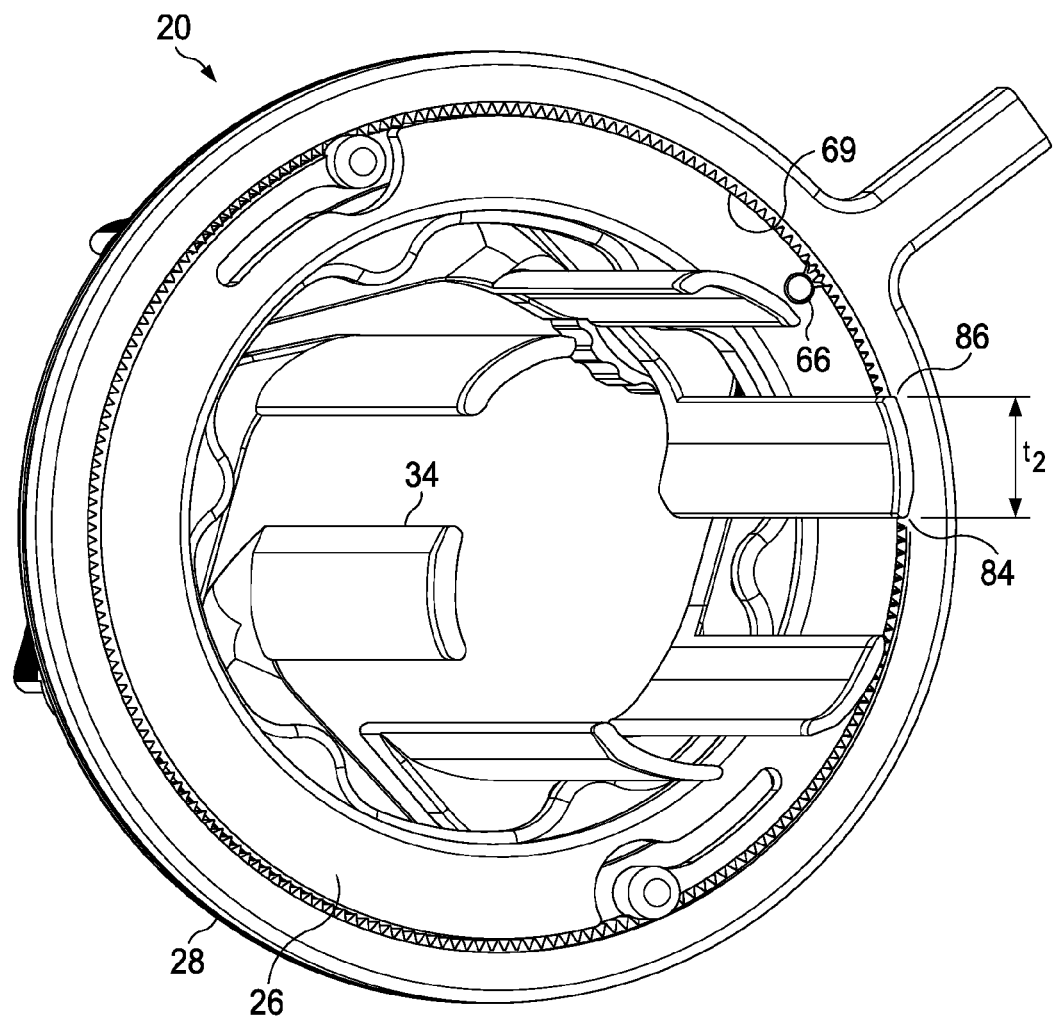
FIG. 8 illustrates a bottom perspective view of a retractor device according to another embodiment of the present disclosure.

Referring to FIGS. 5-6, the arms 30 (and thus the blades 34) are movable from a substantially closed position (FIG. 5) to a substantially open position (FIG. 6). Accordingly, the retractor device 20 may be inserted through a relatively small incision site and then later may be widened to allow access to the operation site. To facilitate such movement, the retractor device 20 includes an actuator 60 that, in some embodiments, has a knob 62 disposed at a distal end of a shaft 64 (as shown in FIG. 2). The actuator 60 further includes a gear 66 for coupling to corresponding teeth 68 disposed along a circumference of the inner ring 26. In embodiments where an additional mounting ring is used (e.g., mounting ring 28 in FIG. 2), the gear 66 may further engage corresponding teeth 69 disposed along a circumference of the mounting ring 28 as is illustrated in FIG. 8. Preferably, the shaft 64 of the actuator 60 is stepped in diameter such that a lower portion adjacent to the gear 66 is smaller in diameter relative to a remaining portion of the shaft. This may accommodate size constraints associated with connection of the shaft 64 to the gear 66, while also providing additional stability to the actuator 60 with the increased diameter portion of the shaft. Referring to FIG. 3, a proximal end of the shaft 64 may include a flange 70 for retaining the actuator 60 within the frame 22.

In practice, the actuator 60 is rotated via rotation of the knob 62. The teeth of gear 66 thus engage the teeth 68 of the inner ring 26 to thereby urge the inner ring in a direction of rotation opposite that of the actuator gear 66. Rotation of inner ring 26 in the direction R (shown in FIGS. 2 and 5) causes translation of the peg 38 along the elongated slot 35 to thereby move the blades from the closed position of FIG. 5 to the open position of FIG. 6. In some embodiments, rotation is only desired in one direction such that the surrounding tissue does not urge the blades 34 back to the closed position of FIG. 5. Accordingly, with reference to FIG. 5, the retractor device 20 further includes a ratchet mechanism 72, which may be a flexible limb integrally formed with the outer ring 24 that bears against the inner ring 26 and engages teeth 73 of the inner ring. In this manner, the ratchet mechanism 72 permits rotation in the desired direction of rotation R when opening the blades 34, while preventing rotation in a direction opposite to R. A ratchet release member 74 is connected to the ratchet mechanism 72, which permits disengagement of the ratchet mechanism from the inner ring 26 to allow for collapse of the blades 34 to the closed position. In particular, the ratchet release member 74 may be actuated in a radially outward direction to disengage the ratchet mechanism 72. To permit such radial movement, a gap 76 may be defined in the outer ring 24 adjacent to the ratchet mechanism 72. Once the blades 34 are in a desired position, the ratchet mechanism 72 may be reengaged by releasing the ratchet release member 74.

As discussed previously, the arm members 30 are removable from the frame 22. During use, it may be desirable to initially couple a set of arm members 30 having relatively thin blades 34. Accordingly, a relatively small incision site can accommodate entry and extension of the blades 34 through tissue adjacent a surgical site. Referring to FIG. 4B, in some embodiments, the blades 34 take on a curved configuration, and thus have a width $t_1$ defined from a first terminal end 80 of the curved blade to a second terminal end 82 of the curved blade. After the blades 34 have been inserted through tissue adjacent the surgical site, the retractor device 20 may be actuated to retract the tissue by actuating the knob 60 as described above.

Given the quick-detachable nature of the arm members 30 with respect to the frame 22, the arm members may be quickly removed and replaced with alternative arm members (relative to arm members having width $t_1$). For example, with reference to FIG. 8, arm members 30 with blades 34 having an increased width may replace the relatively thin blades of other embodiments. As with the blades 34 described in previous embodiments, the blades 34 of FIG. 8 may take on a curved configuration and have a width $t_2$ defined from a first terminal end 84 of the curved blade to a second terminal end 86 of the curved blade. The width $t_2$ is greater than the width $t_1$. In this manner, the wider blades of FIG. 8 may be used to retain retraction without applying as much pressure to patient's tissue as would be applied by less thick blades.

After the spinal segment (or other anatomical structure) is addressed by the surgeon, the arm members 30 may be retracted by actuating the ratchet release member 72. During the process of retraction, the arm members 30 having relatively thick blades (e.g., FIG. 8) may be removed by grasping the detents 44 and lifting the mounting portion 32 off of the mounting posts 40, and thereby the frame 22. Arm members 30 having relatively thin blades (e.g., FIGS. 2-7) may be placed onto the frame 22 by inserting the mounting portion 32 over the mounting posts 40 via the eccentric holes 36 defined through the arm members. In this manner, the retractor device 20 may be removed from the body through a relatively small incision site, thus minimizing tissue damage.

Figure 9A:
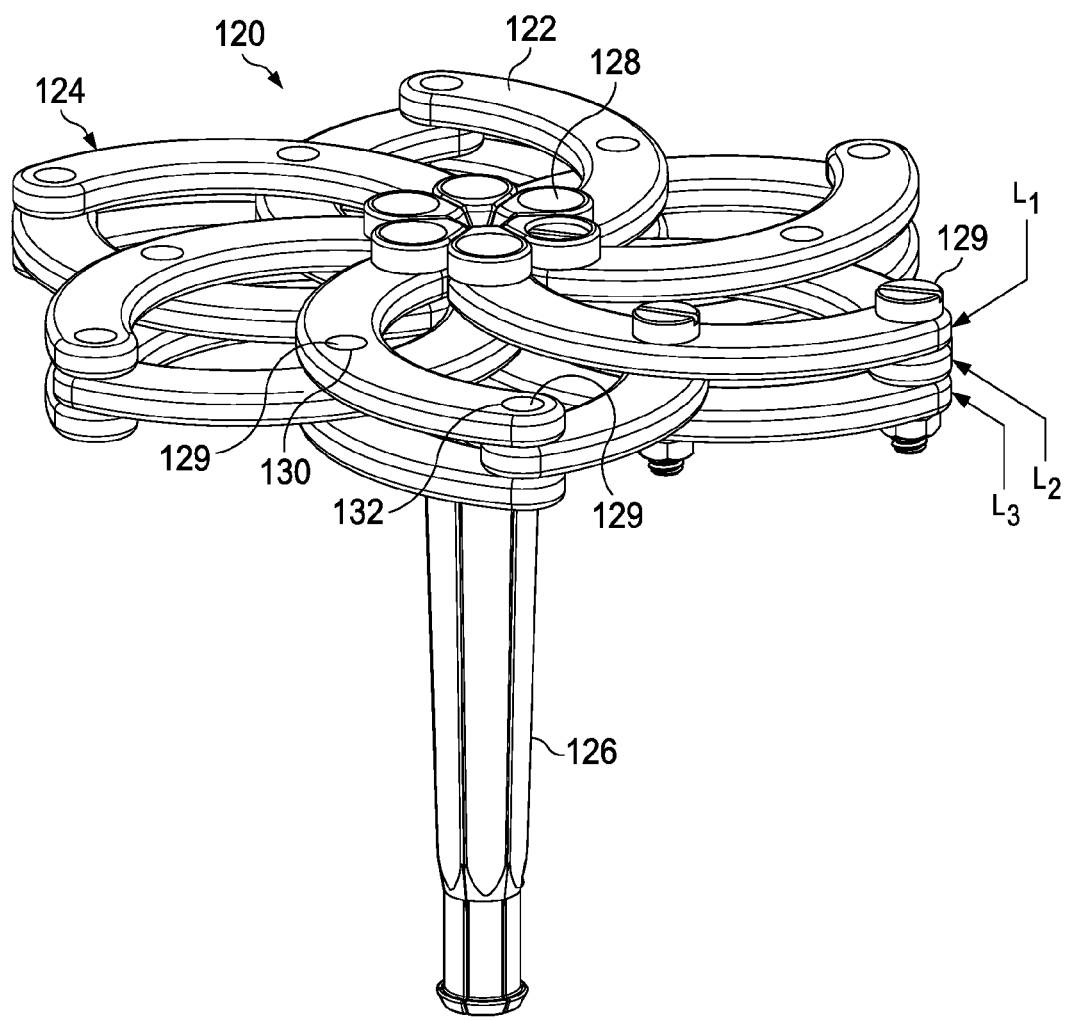
FIG. 9A illustrates a top perspective view of a retractor device with blades in a closed position according to another embodiment of the present disclosure.
Figure 9B:
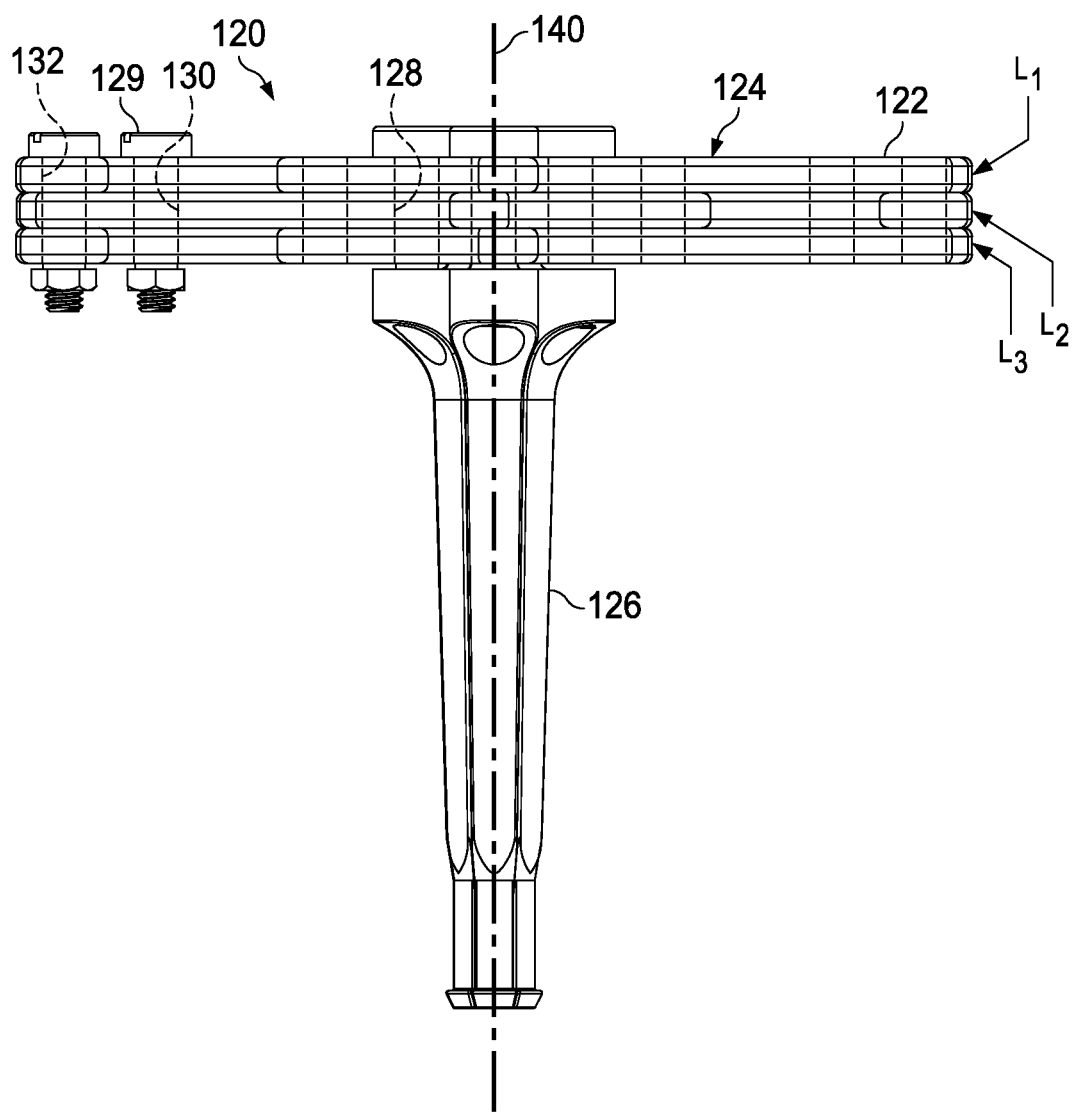
FIG. 9B illustrates a side view of the retractor device of FIG. 9A.
Figure 9C:
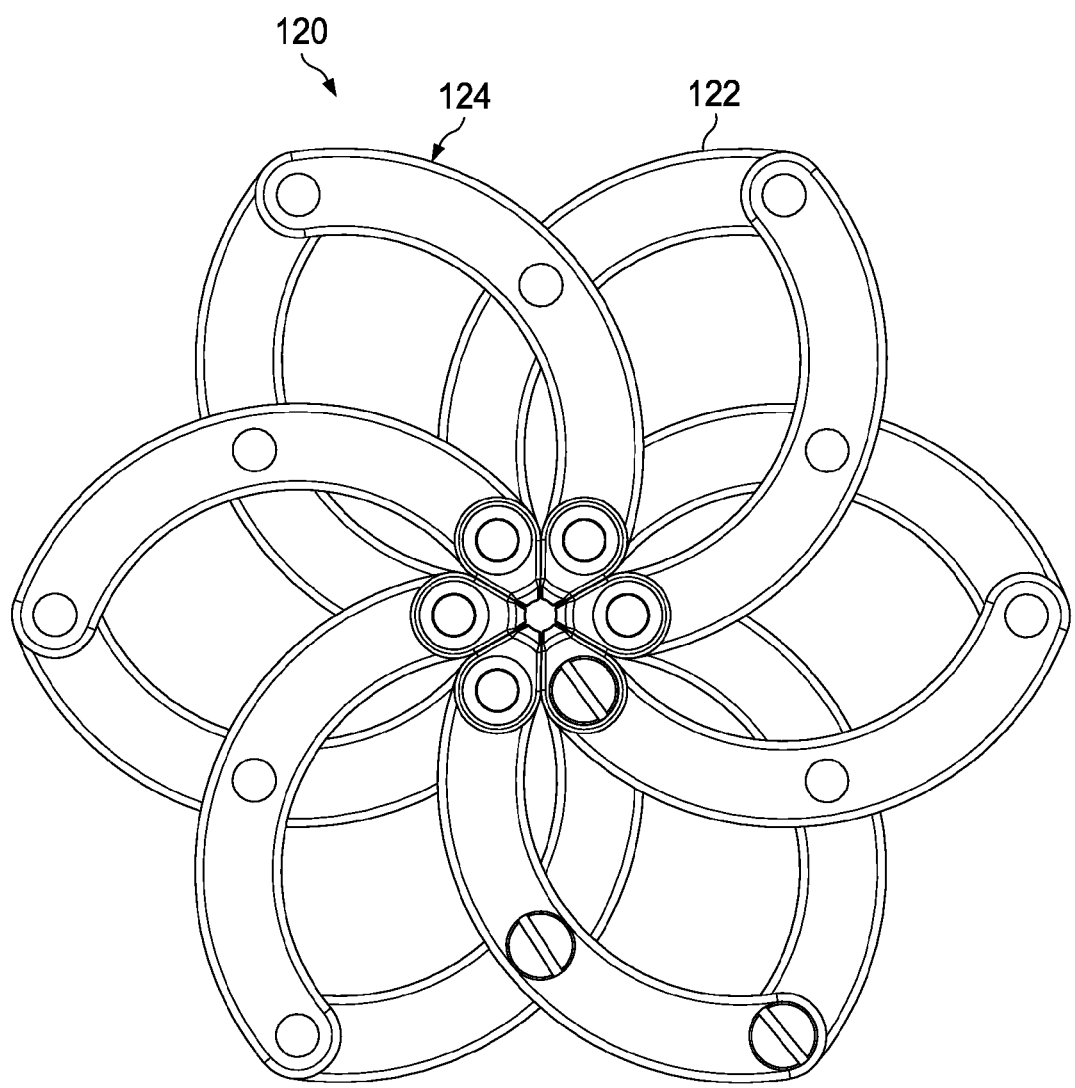
FIG. 9C illustrates a top view of the retractor device of FIG. 9A.
Figure 10A:
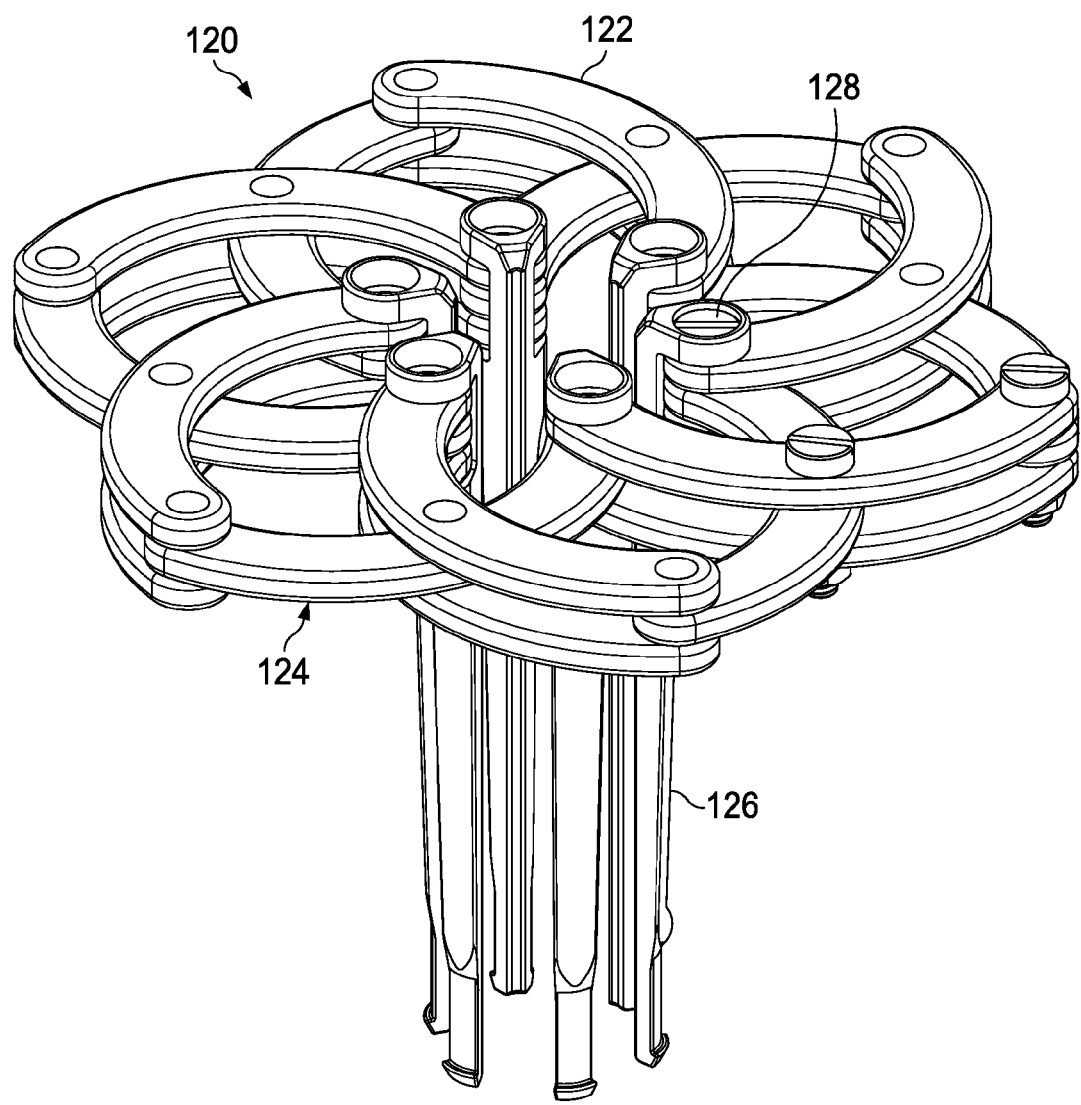
FIG. 10A illustrates a top perspective view of the retractor device of FIG. 9A with the blades in a partially open position.
Figure 10B:
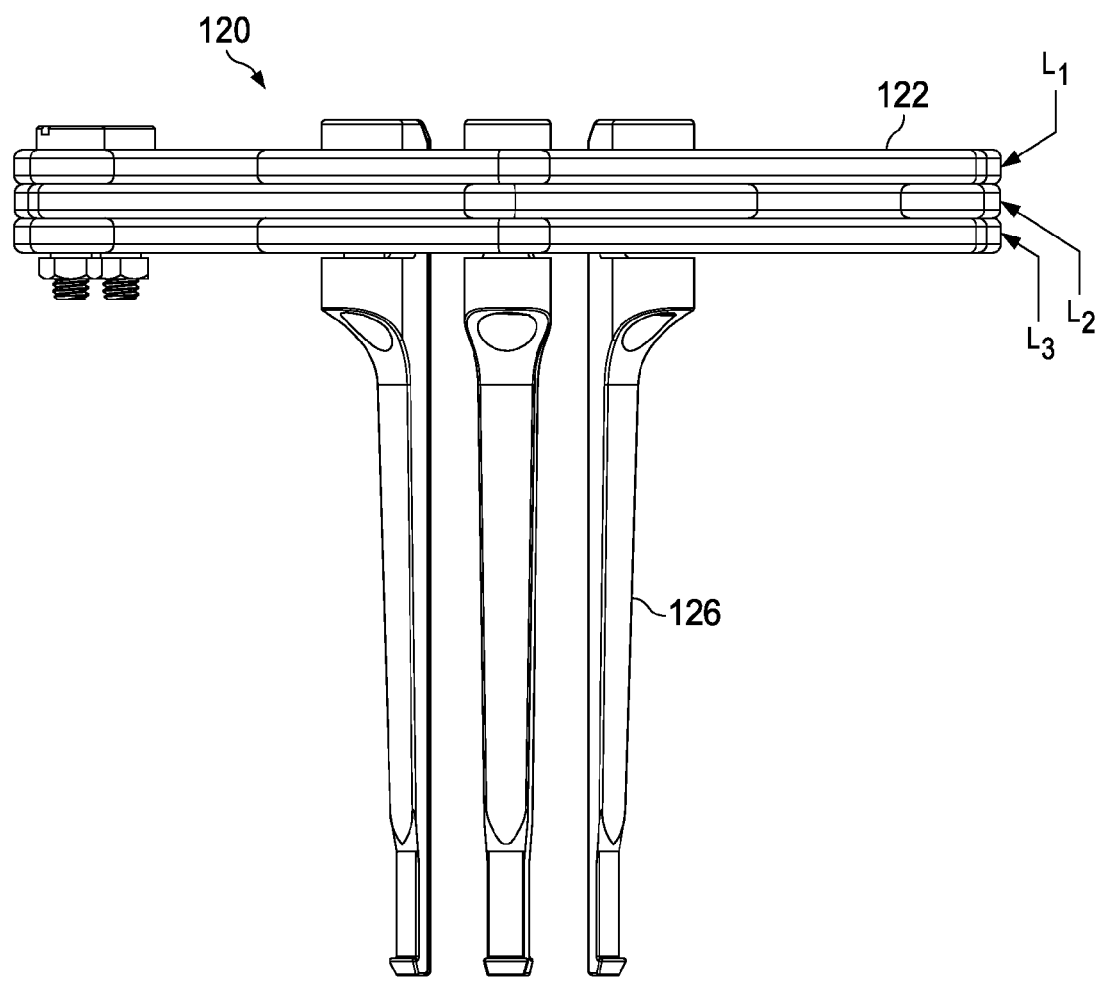
FIG. 10B illustrates a side view of the retractor device of FIG. 10A.
Figure 10C:
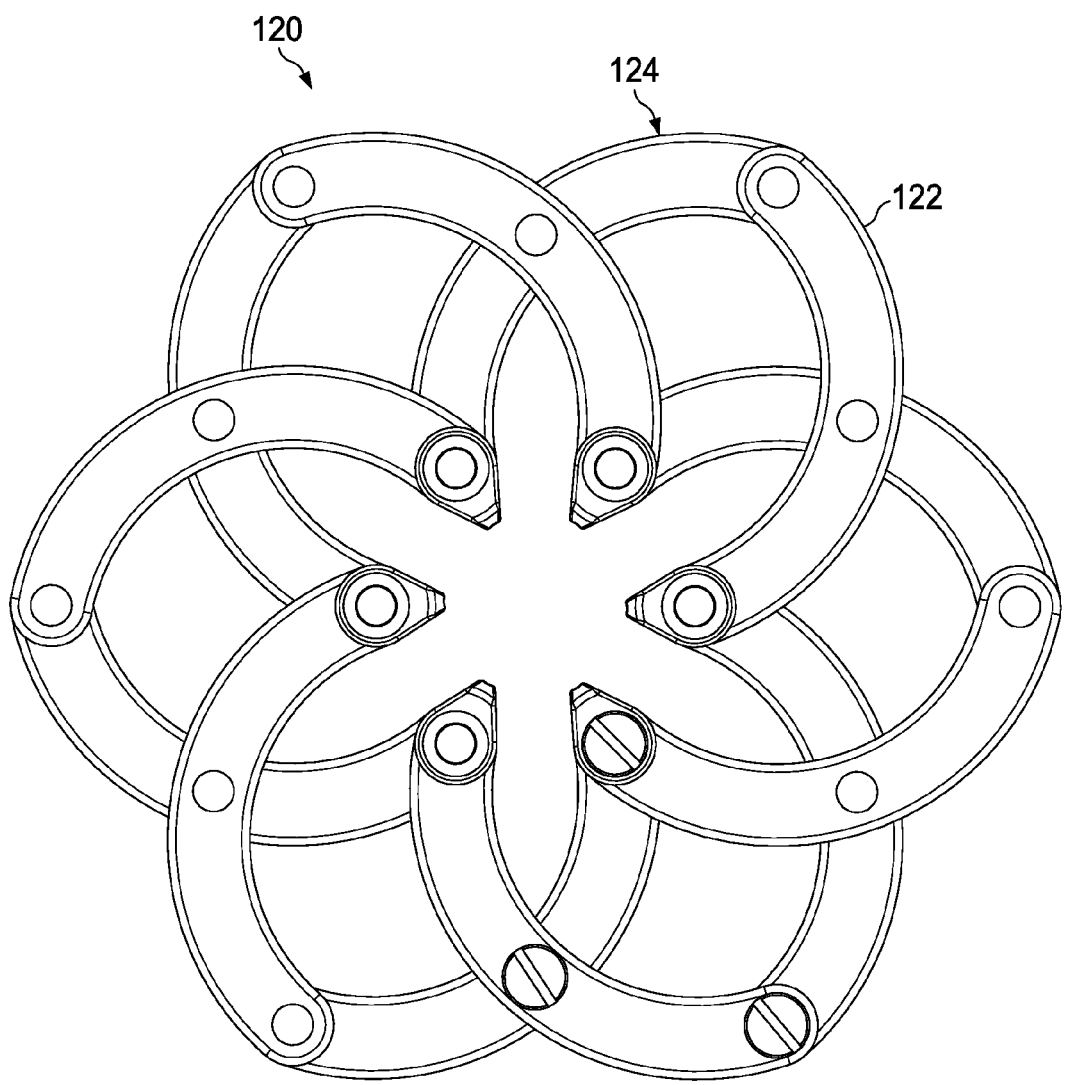
FIG. 10C illustrates a top view of the retractor device of FIG. 10A.
Figure 11A:
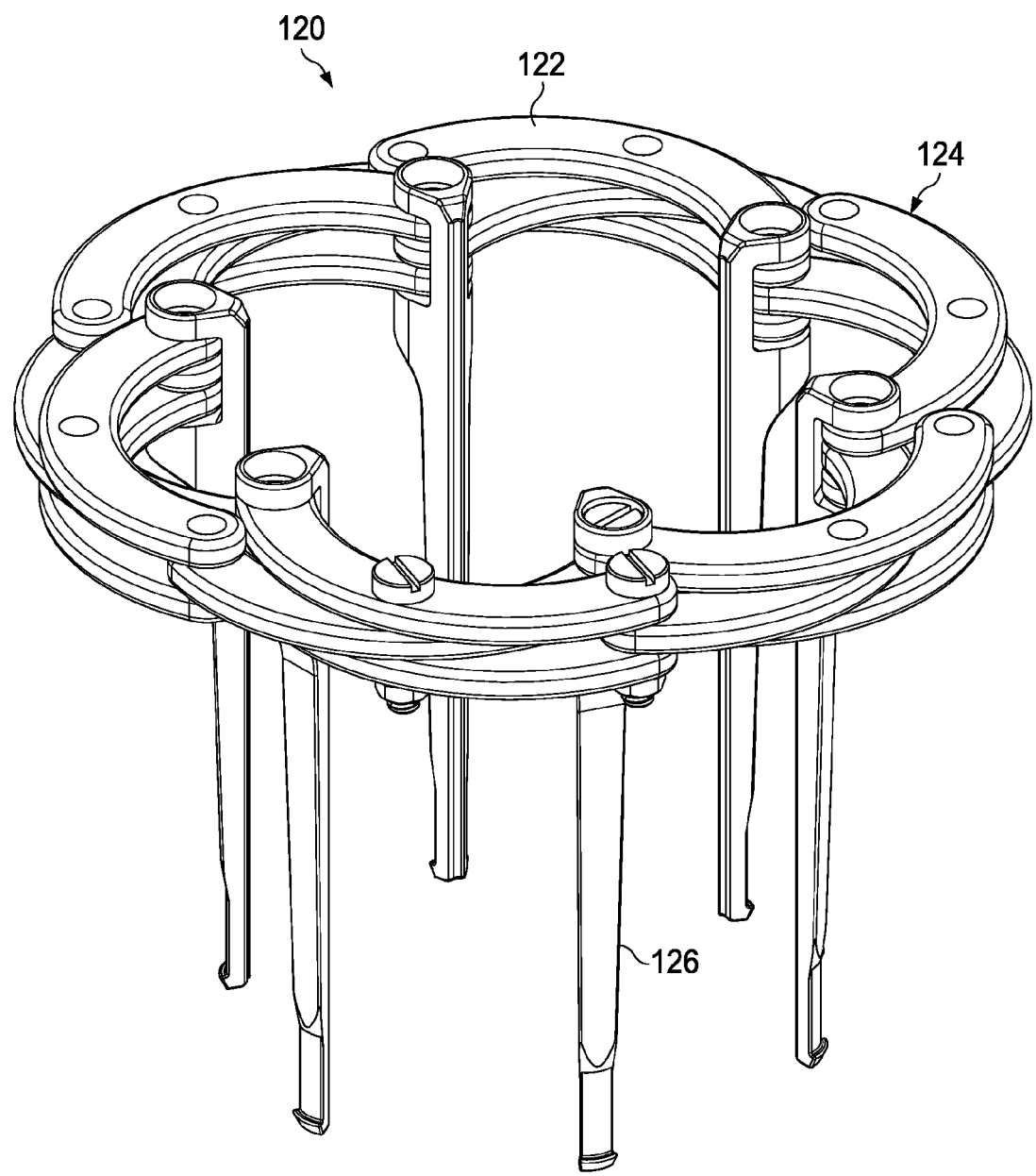
FIG. 11A illustrates a top perspective view of the retractor device of FIG. 9A with the blades in a substantially open position.

FIGS. 9-11 illustrate an alternative retractor device 120 having a plurality of linkages 122, which cooperate to define a frame 124 of the retractor device. A plurality of blades 126 are coupled to the linkages 122 and extend in a direction substantially perpendicular to a plane defined by the frame 124. The linkages cooperate to move the blades 126 from a first position to other positions. For example, the blades may be moved from a substantially closed position (as shown in FIG. 9A) to an intermediate position (as shown in FIG. 10A), and to a substantially open position (as shown in FIG. 11A) as will be described. The blades 126 may be separate members, which are coupled to the linkages 122 via mechanical fasteners 128, such as nuts. For example, a proximal portion of the blade may have a cylindrical shape and be externally threaded. As such, the proximal portion of the blade 126 may pass through a hole defined at an intersection of three linkages 122 and be secured therethrough via the nut 128. Such an arrangement facilitates quick detachment of the blades 126 such that blades of a different size (i.e., length and/or width) may replace the blades initially disposed on the frame 124. In other embodiments, the blades 126 may be integrally formed with the linkages 122 and thus not removable. Also, similar to the blades 34 of the embodiments depicted in FIGS. 1-8, the blades 126 of the embodiments depicted in FIGS. 9-11 may be curved.

The linkages 122 are preferably similar in size and shape and take on a curved configuration. The linkages 122 are interconnected to other linkages via mechanical fasteners 129, such as rivets or screw/nut combinations, which are disposed through intermediate and outer holes 130, 132, respectively, defined through the linkages. For example, with reference to FIG. 9B, each linkage 122 may have three holes defined therethrough. The inner holes 128 may accommodate corresponding blades 124 as described above, while sets of intermediate and outer holes 130, 132 provide remaining points of interconnection for the linkages to complete the frame 124 of the retractor device 120.

More specifically, in some embodiments, the frame 124 of the retractor device 120 includes three layers of linkages. A top layer $L_1$ preferably includes six linkages 122 that are curved in the same direction and generally spiral about a longitudinal axis 140 defined through a center of the blades 126 when the frame is in the closed position (FIG. 9A). For example, the linkages in layer $L_1$ may take on a spiral shape when the frame 124 is in the closed position. An intermediate layer of linkages $L_2$ includes six linkages 122, which are disposed in the frame 124 such that they exhibit an opposite direction of curvature relative to the curvature of the linkages in layer $L_1$. The linkages 122 in layer $L_2$ thus generally spiral about the longitudinal axis 140 in a direction opposite that of the linkages in layer $L_1$. Still further, a bottom layer $L_3$ preferably includes six linkages 122 that are curved in the same direction and substantially in the same manner as the linkages of layer $L_1$. That is, the linkages 122 in layer $L_3$ generally spiral about the longitudinal axis 140 and are longitudinally offset, yet aligned with the linkages in layer $L_1$ to permit interconnection of the layers.

Figure 11B:
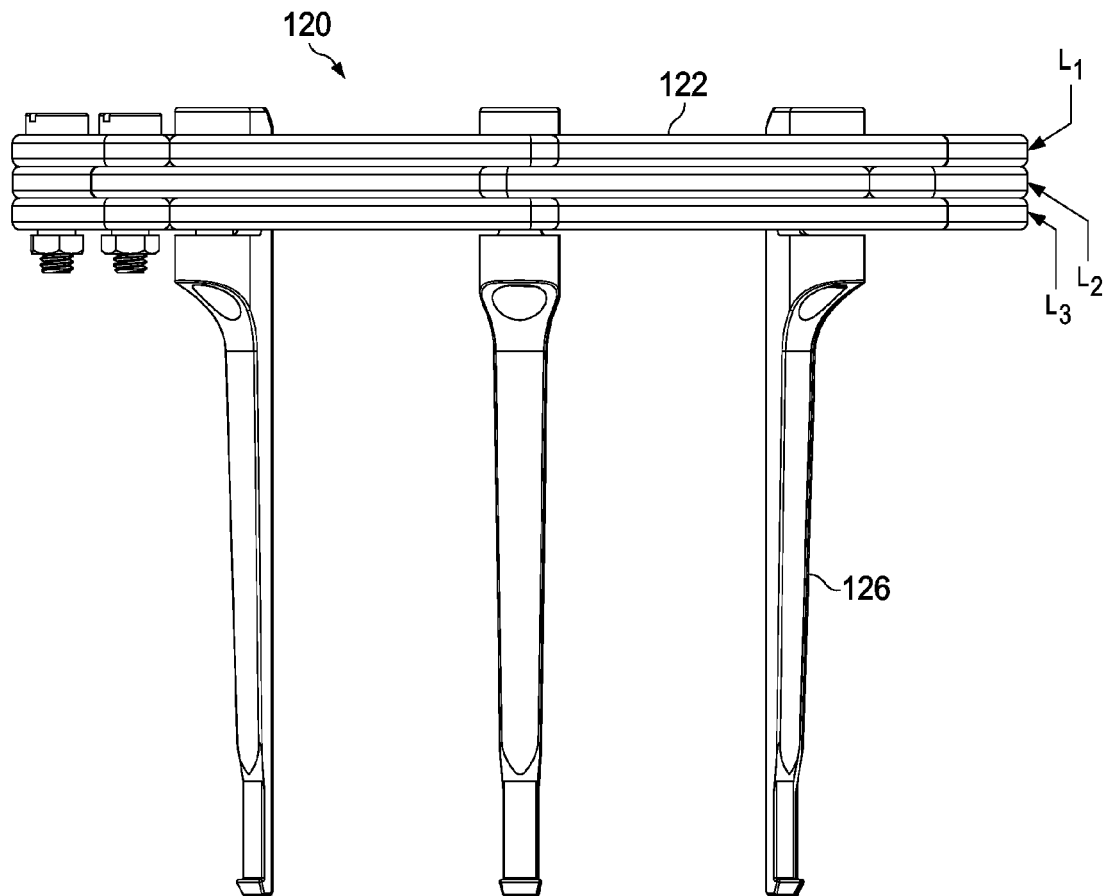
FIG. 11B illustrates a side view of the retractor device of FIG. 11A.
Figure 11C:
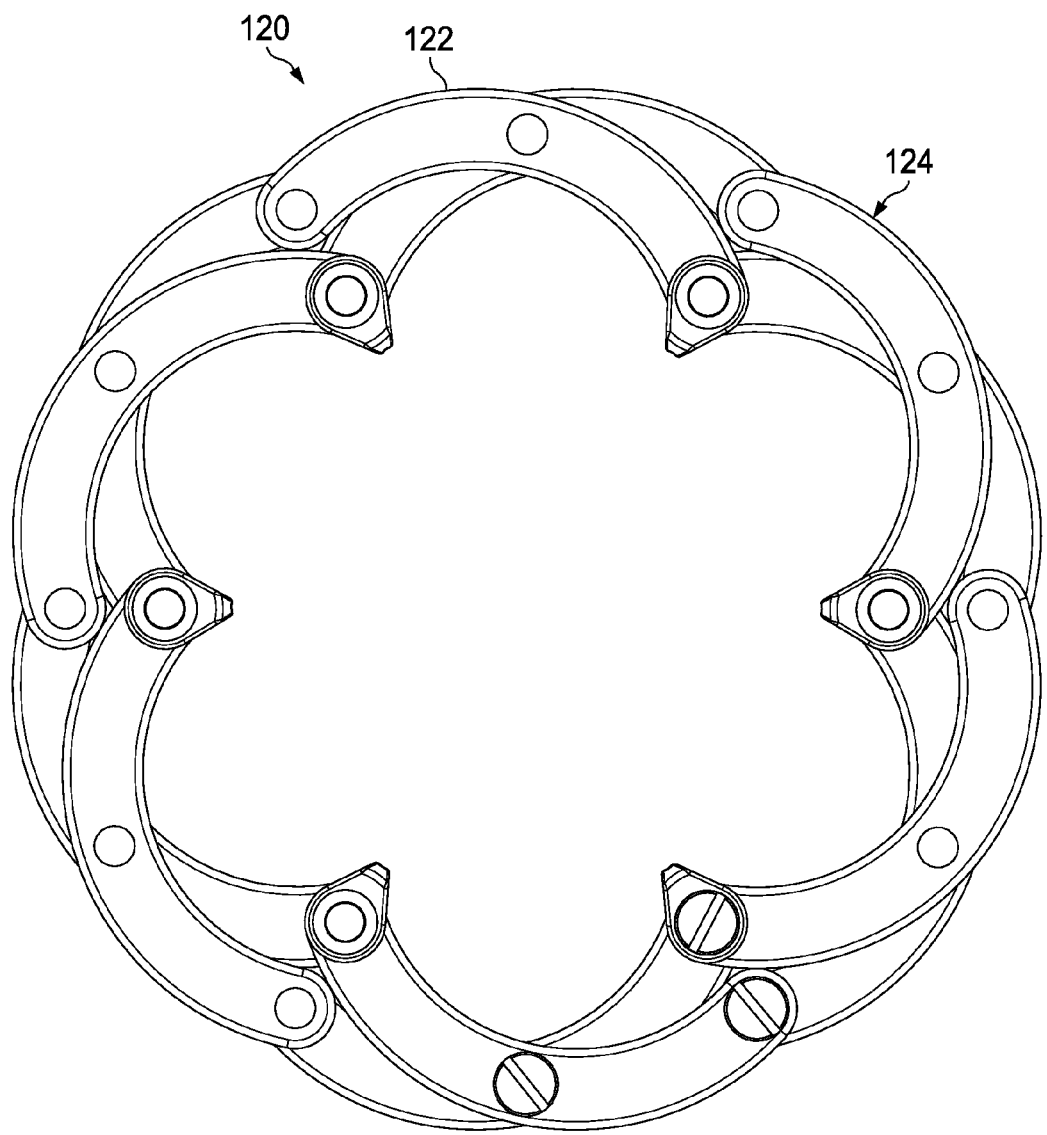
FIG. 11C illustrates a top view of the retractor device of FIG. 11A.

Each layer $L_1$, $L_2$ and $L_3$ preferably includes eighteen points of interconnection along each layer. Of course, other embodiments are contemplated with less or more points of interconnection and less or more layers. Each layer $L_1$, $L_2$ and $L_3$ of linkages is interconnected at the outer and intermediate holes 132, 130, respectively, via mechanical fasteners and is further interconnected at the inner holes via the blades 126. In this manner, movement of one set of layered linkages (e.g., at one interconnection point defined at hole 132) will cause movement of the remainder of the frame 124. Moreover, the layered linkages 122 of the frame 124 are interconnected in such a way that the frame is symmetrical when viewed in plan whether the frame is in a substantially closed position (FIGS. 9A-C), an intermediate position (FIGS. 10A-C), or a substantially open position (FIGS. 11A-C). This arrangement permits the blades 126 to move in a simultaneous manner from a substantially closed position (FIGS. 9A-C) to a substantially open position (FIGS. 11A-C).

Various mechanisms may be used to actuate the retractor device 120. For example, with reference to FIG. 12, a pair of handles 150, 152 may be coupled to one of the mechanical fasteners 129 disposed through one of the outer holes 132. One of the handles 150 may be fixedly coupled to the mechanical fastener 129 in between a linkage 122 of the top layer $L_1$ and a corresponding linkage 122 of the intermediate layer $L_2$. The other handle 152 may be further fixedly coupled to the same mechanical fastener 129 in between the linkage 122 of the intermediate layer $L_2$ and a corresponding linkage of the bottom layer $L_3$. In an initial position in which the frame 124 is substantially closed, the handles may initially extend away from one another. When it is desired to actuate the frame 124, the handle 152 may be manually moved towards the handle 150 to thereby cause the frame to open. More specifically, due to the fixed coupling of the handles 150, 152 to the mechanical fastener 129 passing through the interconnection point, relative actuation of the handles towards one another will urge the corresponding linkages 122 in the top and bottom layers $L_1$, $L_3$, respectively, away from the corresponding linkage in the intermediate layer $L_2$, thereby causing movement of the remainder of the frame 124 in a similar manner.

Figure 12:
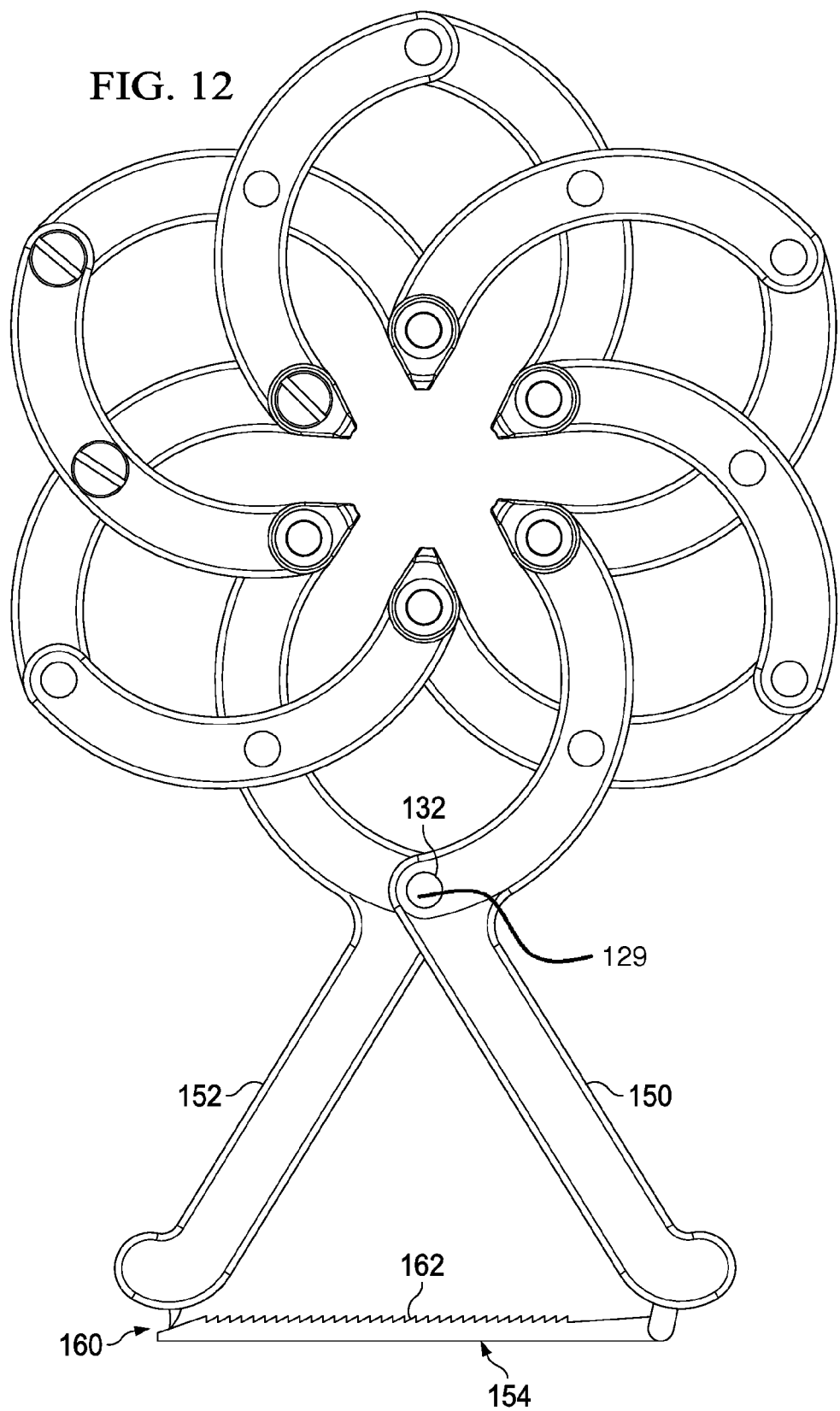
FIG. 12 illustrates a perspective view of a locking device for the retractor device of FIGS. 9-11.

The handles 150, 152 may be used with a locking device 154 equipped with a release mechanism for locking the retractor device 120 at a desired position. In one embodiment, the locking device 154 is a plier-style medical instrument that includes a ratchet mechanism 160 that facilitates opening of the frame 124 while disallowing movement of the blades in the opposite direction. That is, a series of teeth 162 of the ratchet mechanism 160 cooperate with the handle 152 as it is moved toward handle 150 to lock the blades into a desired position. The embodiment of FIG. 12 is presented by way of example only as it is contemplated that other types of actuation and locking mechanisms may be used with the retractor device 120.

In practice, the retractor device 120 may be used to facilitate access to a surgical site through tissue. After the incision is made, the retractor device 120 may be inserted through the incision site (blades 126 first) when the retractor device 120 is in a substantially closed position such as illustrated in FIGS. 9A-C. In a substantially closed position, the blades 126 are grouped together and depend from a center of the frame 124. Once inserted, the retractor device 120 may be actuated to move the frame 124, and therefore the blades 126, from a closed position to a substantially open position such as illustrated in FIGS. 11A-C. Actuation of the retractor device 120 causes the blades 126 to move in a simultaneous manner in an outward direction away from the center of the frame 124, thus retracting the surrounding tissue and providing the surgeon access to the surgical site (e.g., diseased disc). In some embodiments, the blades 126 may be fully retracted to a substantially open position in which the blades are disposed adjacent a circumference of the frame 124. However, other methodologies may call for less retraction, such as an intermediate retraction as illustrated in FIGS. 10A-C. Once the blades 126 are retracted to the desired position, the frame may be locked via the locking device 154. Upon completion of the surgical procedure at the surgical site, the frame may be disengaged from the locked position by actuating a release mechanism associated with the ratchet mechanism 160.

Figure 13A:
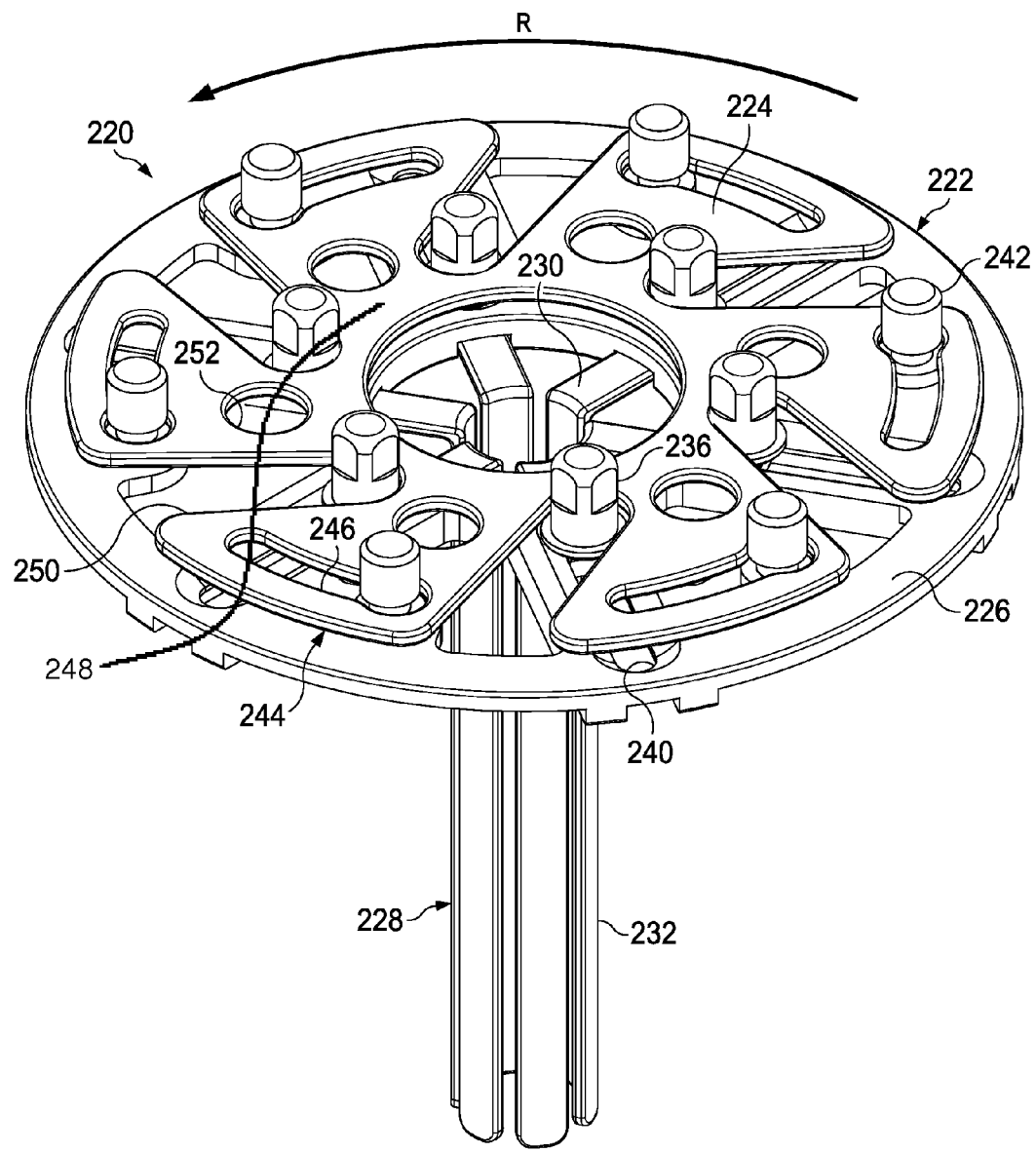
FIG. 13A illustrates a top perspective view of a retractor device with blades in a closed position according to yet another embodiment of the present disclosure.
Figure 13B:
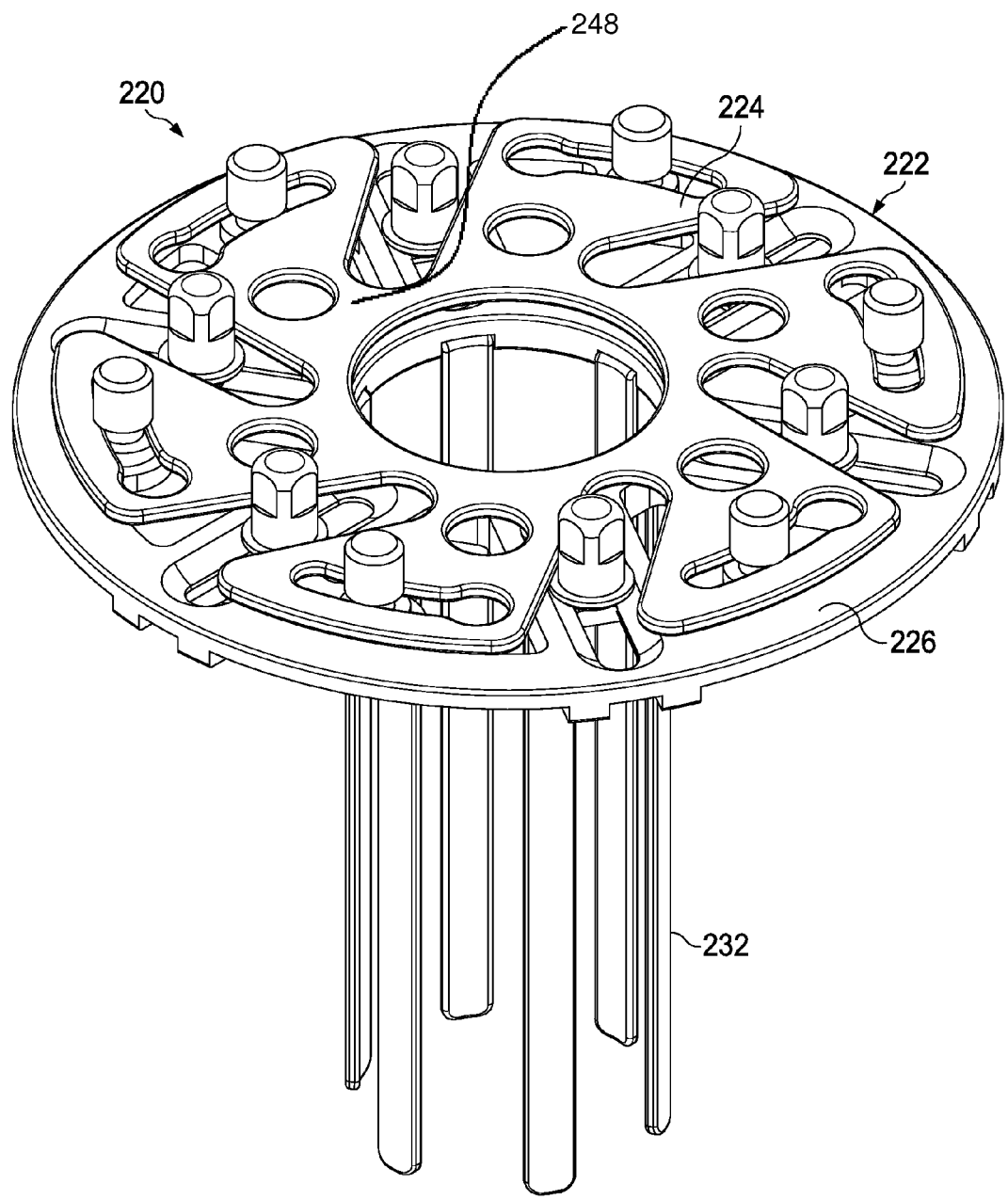
FIG. 13B illustrates a top perspective view of the retractor device of FIG. 13A with blades in a partially open position.
Figure 13C:
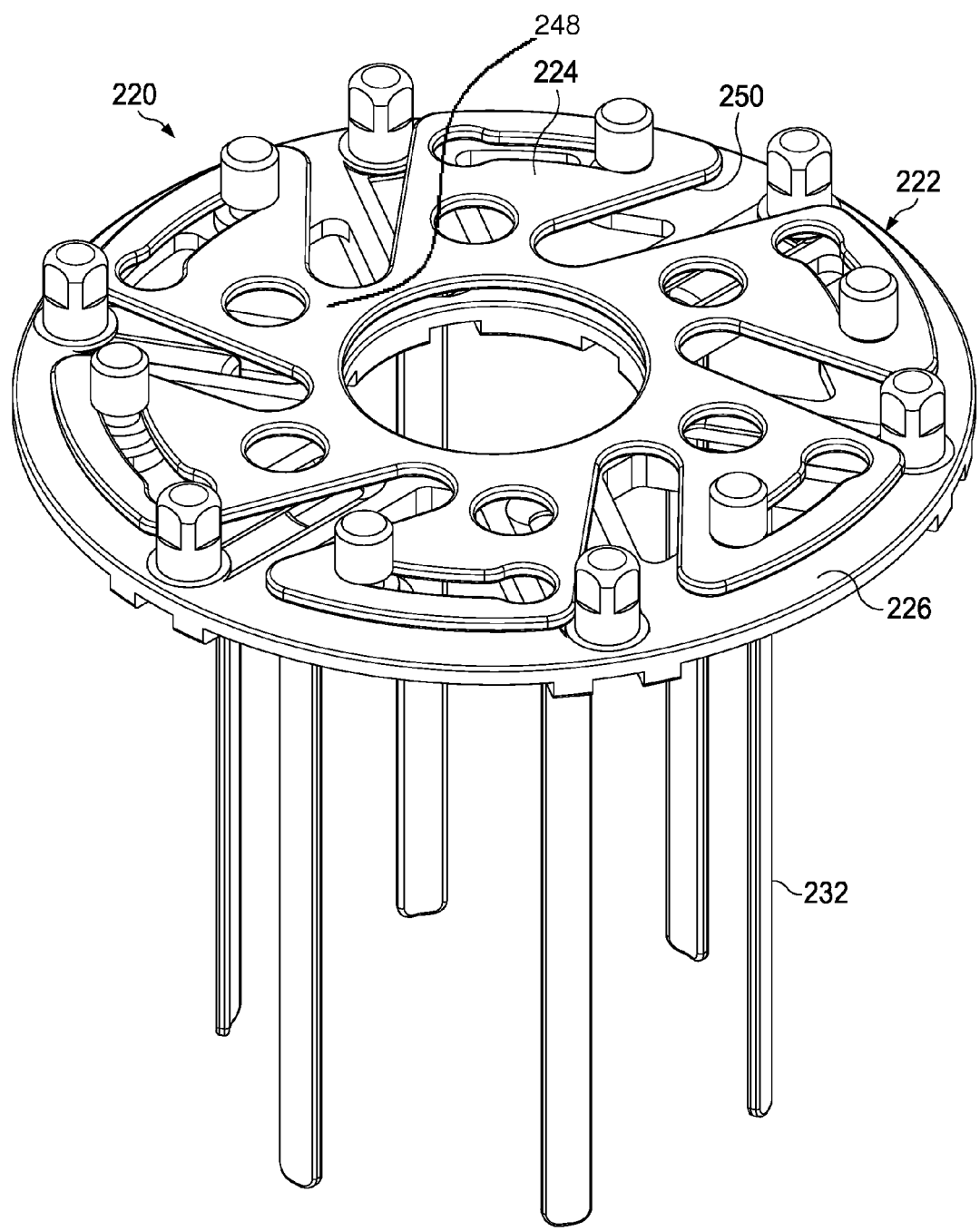
FIG. 13C illustrates a top perspective view of the retractor device of FIG. 13A with blades in a substantially open position.
Figure 14:
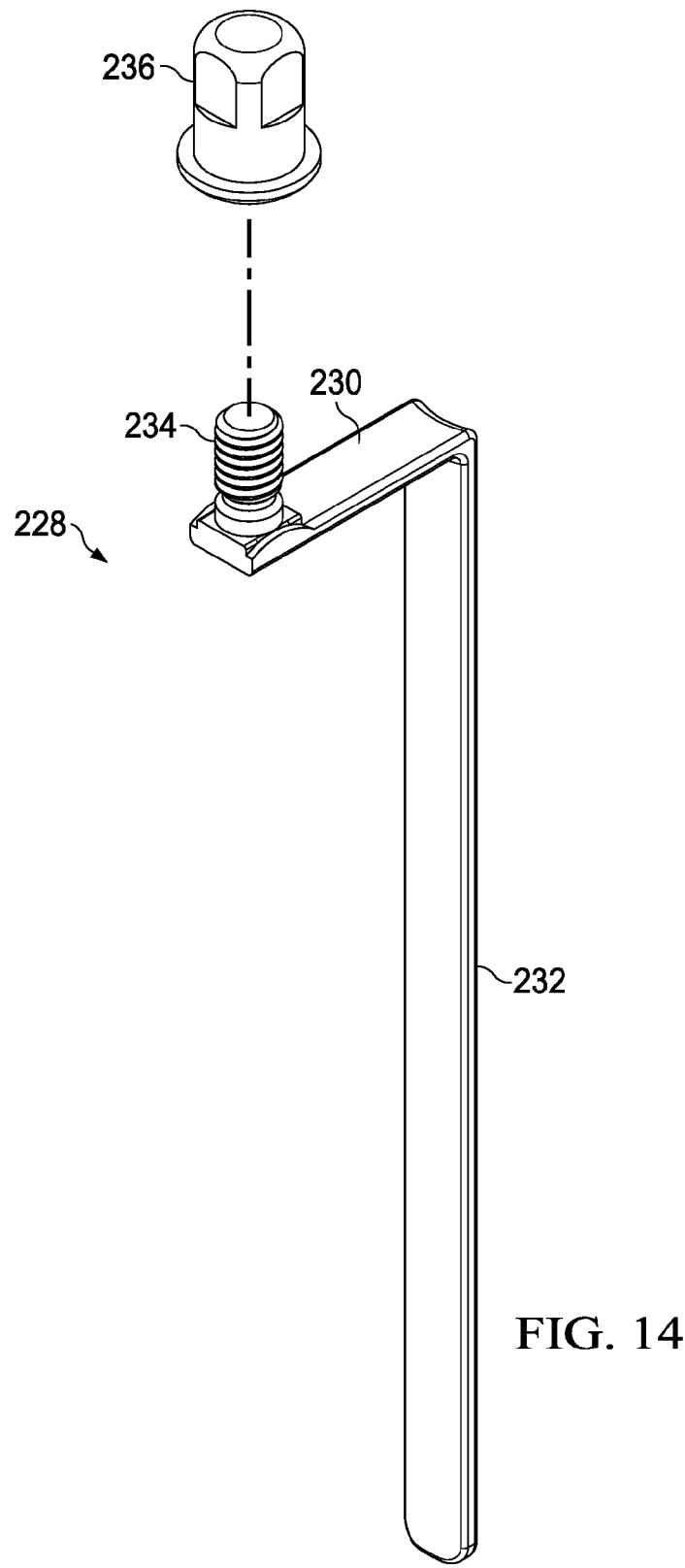
FIG. 14 illustrates a blade of the retractor device of FIG. 13A according to one embodiment of the present disclosure.

FIGS. 13A-C illustrate yet another embodiment of a retractor device 220 according to the principles of the present disclosure. The retractor device 220 includes a frame 222 having an upper disc member 224 disposed over a lower disc member 226. A plurality of arm members 228 are coupled to the frame 222. Referring to FIG. 14, the arm members 228 preferably include a mounting portion 230 and a blade portion 232 coupled with the mounting portion. In some embodiments, the mounting portion 230 and blade portion 232 may be integrally connected, thus comprising a single piece in which the mounting portion extends at a right angle to the blade portion. The mounting portion 230 may further include a threaded post 234 disposed at a distal end of the mounting portion for engaging a mechanical fastener 236, such as a correspondingly threaded nut.

Referring again to FIGS. 13A-C, the lower disc member 226 includes a plurality of channels 240 defined radially therethrough for receiving the mounting portions 230 of the arm members 228. In some embodiments, the nut 236 is of sufficient diameter to retain the mounting portion 230 in the channel 240. The lower disc member 226 further includes a plurality of posts 242 for engaging the upper disc member 224. More specifically, the upper disc member 224 includes a plurality of radially extending tabs 244, which include elongated slots 246 defined therein. The elongated slots 246 are adapted to receive the posts 242 of the lower disc member 226 to thereby align and guide the upper disc member relative to the lower disc member. The tabs 244 extend from a central portion 248 of the upper disc member 224 and increase in size in the radially outward direction to accommodate the elongated slot 246 defined therein, while also defining gaps 250 radially along the upper disc member 224. The upper disc member 224 further defines a plurality of holes 252 radially along the upper disc member.

Figure 15:
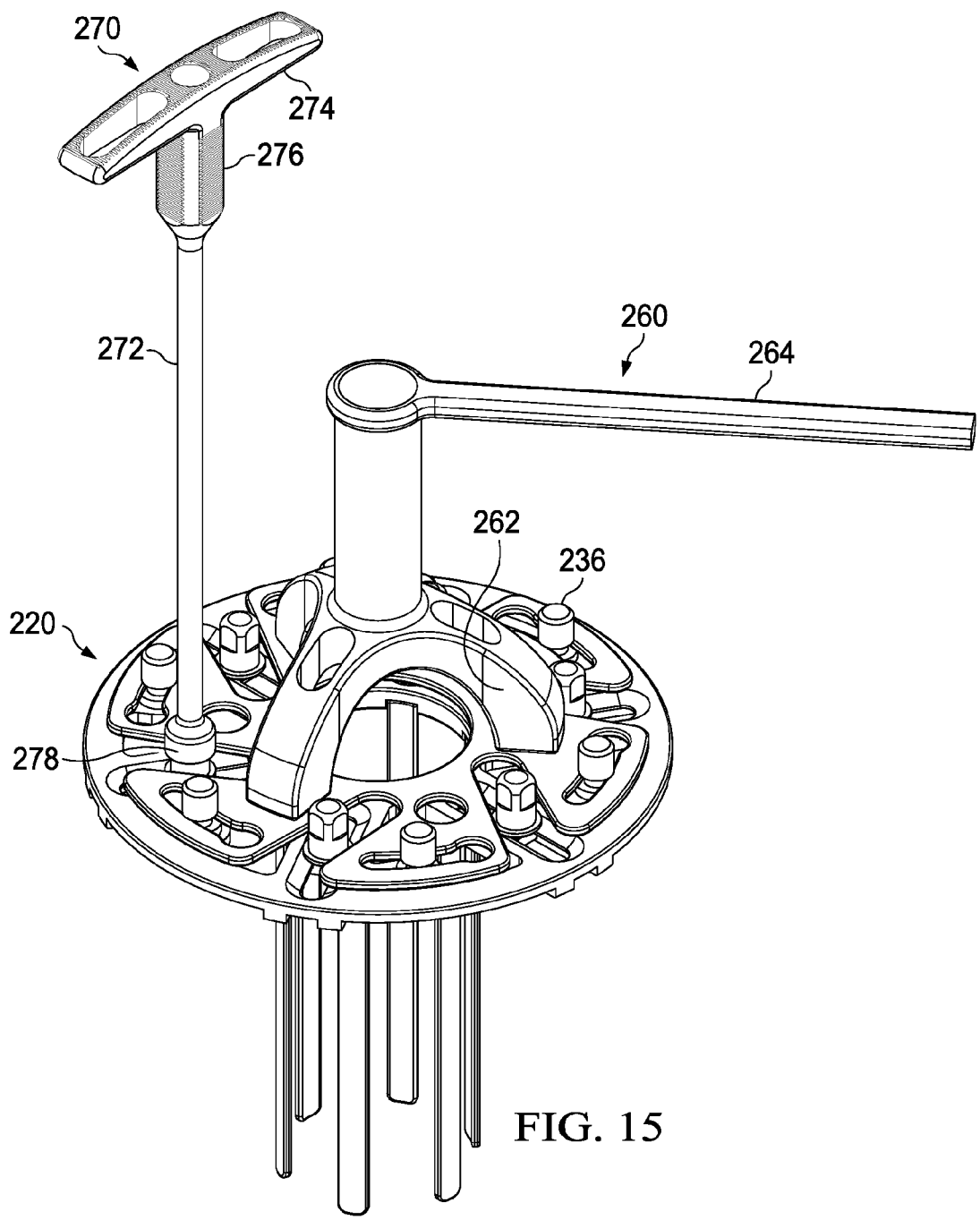
FIG. 15 illustrates a top perspective view of the retractor device of FIG. 13A with a locking tool and rotation tool coupled thereto.

The retractor device 220 permits either simultaneous or independent movement of the blades from a first, substantially closed position (FIG. 13A) to a second, substantially open position (FIG. 13C). In some situations, only partial opening of the blades 232 (FIG. 13B) may be desired. In methodologies where simultaneous actuation of the blades 232 is desired, the upper disc member 224 may be rotated in the direction R as indicated in FIG. 13A. To assist with such rotation, a rotation tool 260 may be used with the retractor device 220 as illustrated in FIG. 15. The rotation tool 260 includes a plurality of arms 262 having distal ends that couple with the upper disc member 224. For example, the arms 262 may have pegs extending therefrom to engage the holes 252 defined radially along the upper disc member 224. Once the rotation tool 260 is engaged with the upper disc member 224, an actuator 264 may be used to impart rotation to the tool, which in turn, imparts rotation to the upper disc member.

By rotating the upper disc member 224 relative to the lower disc member 226, the mounting portions 230 of the arm members 228 are translated along the channel 240 and are guided between the radially extending tabs 244 via the gaps 250 defined therebetween. The posts 242 extending from the lower disc member 226 maintain the upper disc member 224 in the desired alignment relative to the lower disc member during rotation. This is achieved by guiding movement of the upper disc member 224 via the posts 242 along the elongated slots 246. Once the blades 232 are in the desired position, the retractor device 220 may be locked using a locking tool 270 as depicted in FIG. 15. The locking tool 270 may include a shaft 272 with a handle 274 disposed at a proximal end 276 of the locking tool. The locking tool 270 further includes a socket 278 that mates with mechanical fastener 236. The locking tool 270 may be actuated to thereby rotate the socket 278, which in turn, rotates the mechanical fastener 236 to thereby lock the retractor device.

Figure 16:
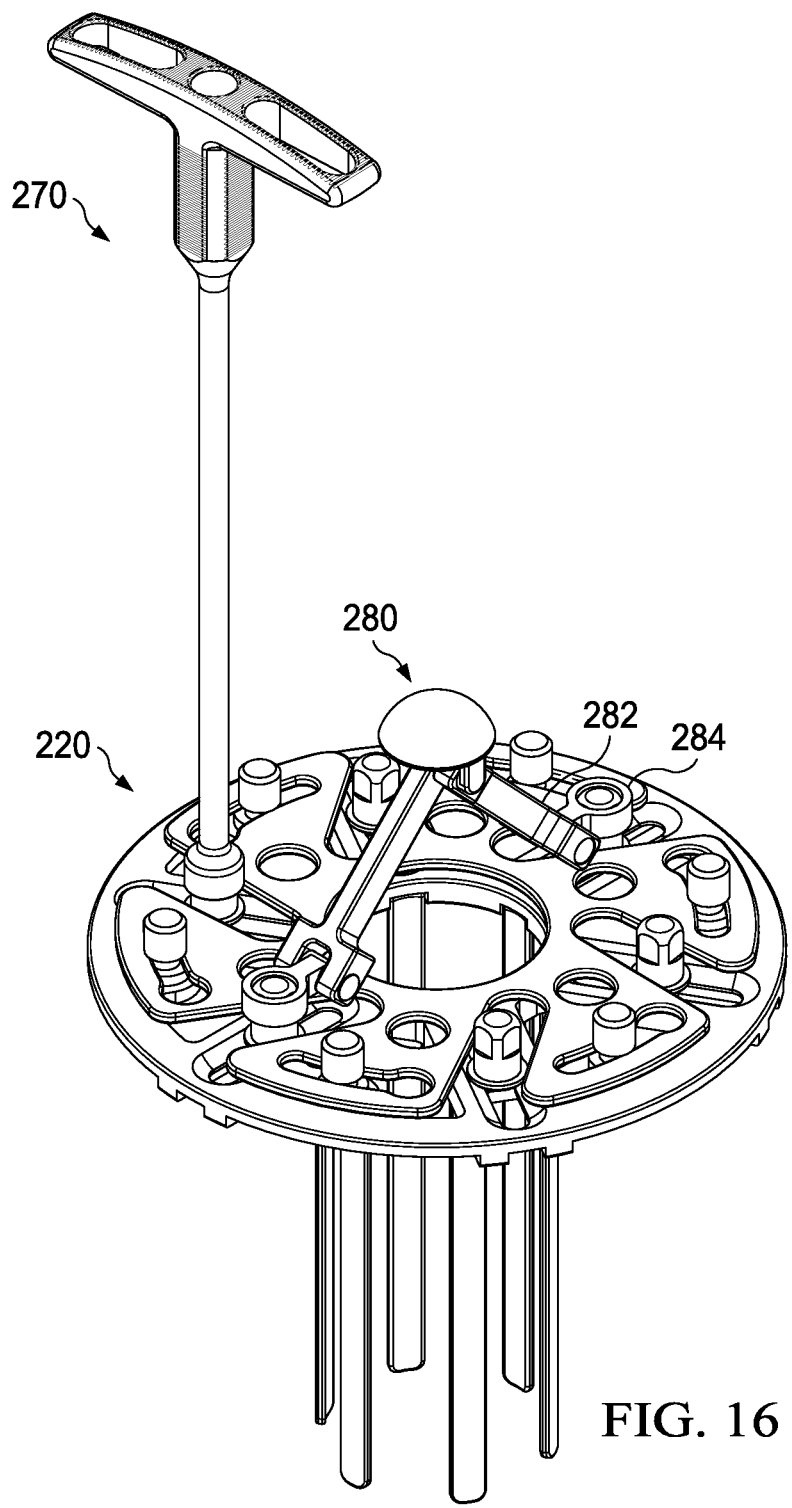
FIG. 16 illustrates a top perspective view of the retractor device of FIG. 13A with a locking tool and a translation tool coupled thereto.

In methodologies where independent movement is desired, individual mounting portions 230 may be manually translated along their corresponding channels 240. To assist with such movement, a translation tool 280 may be used in cooperation with the retractor device 220 as depicted in FIG. 16. The retractor device 220 defines gaps between the mechanical fastener 236 and the radially extending tabs 244 of the upper disc member 224. As such, there is sufficient space to translate blades 232 independently. Accordingly, the translation tool 280 may include a pair of arms 282 with sockets 284 disposed at the distal ends of the arms. One of the sockets 284 may be coupled to one of the posts 242 of the lower disc member 226, while the other socket 284 may be coupled to one of the mechanical fasteners 236. In this manner, the arm 282 corresponding to the engaged mechanical fastener may be actuated to impart independent translational movement to the blade 232 associated with such mechanical fastener. The locking tool 270 may then be used to lock the retractor device as described above with reference to FIG. 15.

While various embodiments of a retractor device and related methods of using such devices have been described above, it should be understood that they have been presented by way of example only, and not limitation. Thus, the breadth and scope of the present disclosure should not be limited by any of the above-described exemplary embodiments, but should be defined only in accordance with the following claims and their equivalents. Moreover, the above advantages and features are provided in described embodiments, but shall not limit the application of the claims to processes and structures accomplishing any or all of the above advantages.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Technical Field," the claims should not be limited by the language chosen under this heading to describe the so-called technical field. Further, a description of a technology in the "Background" is not to be construed as an admission that technology is prior art to any invention(s) in this disclosure. Neither is the "Brief Summary" to be considered as a characterization of the invention(s) set forth in the claims found herein. Furthermore, any reference in this disclosure to "invention" in the singular should not be used to argue that there is only a single point of novelty claimed in this disclosure. Multiple inventions may be set forth according to the limitations of the multiple claims associated with this disclosure, and the claims accordingly define the invention(s), and their equivalents, that are protected thereby. In all instances, the scope of the claims shall be considered on their own merits in light of the specification, but should not be constrained by the headings set forth herein.

What is claimed is:

1. A retractor device, comprising:
    a frame having an inner ring coupled to an outer ring, the inner ring including a plurality of teeth and pegs, the outer ring including a plurality of mounting posts;
    a plurality of arm members, each arm member having a mounting portion that pivotally couples to one mounting post of the outer ring of the frame and a blade portion extending from the mounting portion, wherein each arm member is removably attached to the frame; and
    an actuator that actuates the inner ring such that the inner ring moves relative to the outer ring to thereby pivot the plurality of arm members from a first position to a second position, the actuator including a gear that engages the teeth of the inner ring, and an axis of rotation of the gear being parallel with an axis of rotation of the inner ring, wherein
    the mounting portion of each arm member includes a hole and an elongated slot respectively defined therethrough,
    the mounting post is disposed in the hole,
    the peg is disposed in the elongated slot,
    the gear is disposed about a shaft of the actuator, and
    the shaft is coupled to the gear such that rotation of the shaft causes the gear to rotate about the axis of rotation that is parallel with the axis of rotation of the inner ring.

2. A retractor device according to claim 1, wherein the plurality of mounting posts each include a shaft portion and a head portion, and further wherein the head portion has a greater diameter than the shaft.

3. A retractor device according to claim 2, wherein the mounting post is disposed through the hole to thereby retain the mounting portion to the outer ring.

4. A retractor device according to claim 3, wherein the shaft portion bears against the mounting portion and the head portion is disposed over the mounting portion.

5. A retractor device according to claim 1, wherein the pegs extend from the inner ring.

6. A retractor device according to claim 5, wherein the peg is disposed through the elongated slot and adapted to translate along the elongated slot.

7. A retractor device according to claim 1, wherein the mounting portion comprises a spring-loaded latch member and a pair of detents extending from the latch member.

8. A retractor device according to claim 1, wherein the gear is disposed about a shaft of the actuator, the driving gear adapted to engage the teeth defined along an outer circumferential surface of the inner ring.

9. A retractor device according to claim 1, further comprising a mounting ring disposed about the inner and outer rings, the mounting ring including a handle coupled thereto.

10. A retractor device according to claim 1, wherein each arm member has a mounting portion and a blade portion, the blade portions extending substantially orthogonally to the mounting portions.

11. A retractor device according to claim 1, further comprising a ratchet mechanism that permits the inner ring to move in a first direction and preventing the inner ring from moving in a direction opposing the first direction.

12. A retractor device according to claim 1, wherein the teeth of the inner ring are formed on a radially inward side of the inner ring.

13. A retractor device according to claim 12, wherein the gear of the actuator is disposed on a radially inward side of the inner ring.

14. A retractor device according to claim 1, wherein a knob is disposed on the shaft.

15. A retractor device, comprising:
    a frame having an inner ring coupled to an outer ring, the inner ring including a plurality of teeth and a plurality of pegs, the outer ring including a plurality of mounting posts;
    a plurality of arm members, each arm member having a mounting portion and a blade portion, wherein each mounting portion pivotally couples to one peg of the inner ring and one mounting post of the outer ring of the frame, and wherein each arm member is removably attached to the frame; and an actuator that actuates one of the inner and outer rings such that the plurality of arm members pivot from a first position to a second position, the actuator including a gear that engages the teeth of the inner ring, and an axis of rotation of the gear being parallel with an axis of rotation of the inner ring, wherein the mounting portion of each arm member includes a hole and an elongated slot respectively defined therethrough, the mounting post is disposed in the hole, the peg is disposed in the elongated slot, the gear is disposed about a shaft of the actuator, and the shaft is coupled to the gear such that rotation of the shaft causes the gear to rotate about the axis of rotation that is parallel with the axis of rotation of the inner ring.

16. A retractor device according to claim 15, wherein each of the plurality of arm members includes a mounting portion and a blade portion, the mounting portions being fixedly coupled to the outer ring at substantially equidistant radial spacing.

17. A retractor device according to claim 16, wherein the mounting portions are further movably coupled to the inner ring at substantially equidistant radial spacing.

18. A retractor device according to claim 17, wherein the pegs extending from the inner ring and the mounting posts extend from the outer ring, the pegs and mounting posts being disposed through the mounting portions to thereby couple the plurality of arm members to the inner and outer rings.

19. A method for using a retractor device, comprising:
providing a retractor device having a frame comprising an inner ring coupled to an outer ring, the inner ring including a plurality of teeth and a plurality of pegs, the outer ring including a plurality of mounting posts, the retractor device further comprising a plurality of arm members pivotally coupled to the plurality of mounting posts of the outer ring of the frame, each arm member including a blade portion extending in a direction substantially orthogonal to the frame, wherein the mounting portion of each arm member includes a hole and an elongated slot respectively defined therethrough, the mounting post is disposed in the hole, the peg is disposed in the elongated slot, each arm member is removably attached to the frame, and the gear is disposed about a shaft of the actuator;

actuating, using a gear that engages the teeth of the inner ring, an actuator to impart relative movement between the inner ring and outer ring to thereby pivot the plurality of arm members from a first position to a second position, an axis of rotation of the gear being parallel with an axis of rotation of the inner ring by rotating the shaft of the actuator thereby causing rotation of the gear.

20. A method according to claim 19, wherein the mounting portions are respectively coupled to the inner ring via the pegs extending from the inner ring, and wherein the method further comprises actuating the frame to cause translation of the pegs along the elongated slot.

21. A method according to claim 19, wherein the step of actuating comprises rotating the actuator to impart rotation to the inner ring.

22. A method according to claim 19, wherein the blade portions define an opening therethrough, and wherein the step of actuating comprises increasing the size of the opening.

23. A method according to claim 22, further comprising engaging a release button to decrease the size of the opening.

* * * * *